US012384627B2

(12) United States Patent
Terzini et al.

(10) Patent No.: US 12,384,627 B2
(45) Date of Patent: Aug. 12, 2025

(54) MODULAR PRODUCT DISPENSING AND VERIFICATION SYSTEM AND METHOD

(71) Applicant: Tension International, Inc., Kansas City, MO (US)

(72) Inventors: Robert Terzini, Corinth, TX (US); Kenneth S. Myers, Kansas City, MO (US)

(73) Assignee: Tension International, Inc., Kansas City, MO (US)

( * ) Notice: Subject to any disclaimer, the term of this patent is extended or adjusted under 35 U.S.C. 154(b) by 18 days.

(21) Appl. No.: 18/434,325

(22) Filed: Feb. 6, 2024

(65) Prior Publication Data

US 2024/0174447 A1  May 30, 2024

Related U.S. Application Data

(63) Continuation of application No. 17/827,389, filed on May 27, 2022, now Pat. No. 11,912,506, which is a
(Continued)

(51) Int. Cl.
*B65B 35/10* (2006.01)
*B65B 5/08* (2006.01)
(Continued)

(52) U.S. Cl.
CPC .............. *B65G 1/1378* (2013.01); *B65B 5/08* (2013.01); *B65B 35/10* (2013.01); *B65B 65/003* (2013.01);
(Continued)

(58) Field of Classification Search
CPC ........... B65B 5/08; B65B 35/10; B65B 57/10; B65B 65/003; B65B 67/02; B65G 1/1373;
(Continued)

(56) References Cited

U.S. PATENT DOCUMENTS 2,715,950 A * 8/1955 Law .................. B65G 1/06
221/9
5,096,090 A   3/1992 Schwartz et al.
(Continued)

FOREIGN PATENT DOCUMENTS

| DE | 10332538 A1 | 2/2005 |
| EP | 0494014 A1 | 7/1992 |
| JP | H07155364 A | 6/1995 |

OTHER PUBLICATIONS

Non-Final Office Action dated Jul. 17, 2019, issued in U.S. Appl. No. 15/472,129, 59 pages.
(Continued)

*Primary Examiner* — Stephen F. Gerrity
(74) *Attorney, Agent, or Firm* — Jing He; Polsinelli PC

(57) ABSTRACT

A modular, scalable prescription dispensing and verification system includes a four-tiered central conveyor, dispensing control system with stored patient orders for creating dispensing and routing itineraries, carriers transporting itineraries and dispensed medications, induction station, pairs of processing stations divided by the conveyor, including automated and manual dispensing, verification, cold chain, and ambient packaging. Crossover conveyors transport carriers between dispensing station pair members for dispensing multiple products per station pair. One conveyor tier returns empty carriers to induction, another transports carriers from each dispensing station to verification, then to packaging, another transports carriers from induction to dispensing, then to additional dispensing, another conveys carriers from induction to dispensing stations. Carrier stops halt carriers at stations for removal for processing, replacement, and transport to the next station, or deposit on another tier and transport to a different station. The system may include two
(Continued)

conveyor modules, one for refrigerated or ambient unit-of-use items, another for ambient countables.

20 Claims, 16 Drawing Sheets

Related U.S. Application Data continuation of application No. 16/856,157, filed on Apr. 23, 2020, now Pat. No. 11,345,547, which is a continuation of application No. 15/472,129, filed on Mar. 28, 2017, now Pat. No. 10,669,098.

(60) Provisional application No. 62/314,115, filed on Mar. 28, 2016.

(51) Int. Cl.
| | |
|---|---|
| *B65B 57/10* | (2006.01) |
| *B65B 65/00* | (2006.01) |
| *B65B 67/02* | (2006.01) |
| *B65G 1/137* | (2006.01) |
| *B65G 15/02* | (2006.01) |
| *B65G 43/00* | (2006.01) |
| *B65G 47/50* | (2006.01) |
| *G16H 20/13* | (2018.01) |

(52) U.S. Cl.
CPC .............. *B65B 67/02* (2013.01); *B65G 15/02* (2013.01); *B65G 43/00* (2013.01); *B65G 47/50* (2013.01); *G16H 20/13* (2018.01); *B65B 57/10* (2013.01); *B65G 2201/0258* (2013.01)

(58) Field of Classification Search
CPC .... B65G 1/1376; B65G 1/1378; B65G 15/02; B65G 43/00; B65G 47/50; B65G 2201/0258
USPC .................................................. 53/154, 391
See application file for complete search history.

(56) References Cited

U.S. PATENT DOCUMENTS

| | | |
|---|---|---|
| 5,604,692 A | 2/1997 | Yuyama |
| 7,918,402 B2 | 4/2011 | Conlon et al. |
| 8,215,543 B2* | 7/2012 | Carson et al. ...... G07F 11/1657 235/375 |
| 9,315,323 B2* | 4/2016 | Schubilske .......... G06Q 10/087 |
| 9,394,107 B1 | 7/2016 | Eller et al. |
| 9,409,711 B1 | 8/2016 | Hanssen et al. |
| 9,639,668 B2 | 5/2017 | Joplin |
| 10,669,098 B1 | 6/2020 | Terzini et al. |
| 11,345,547 B1 | 5/2022 | Terzini et al. |
| 2004/0065053 A1 | 4/2004 | Rice et al. |
| 2004/0260424 A1 | 12/2004 | Mahar |
| 2005/0171813 A1 | 8/2005 | Jordan |
| 2006/0177290 A1 | 8/2006 | Freudelsperger |
| 2009/0173779 A1 | 7/2009 | Szesko et al. |
| 2010/0172724 A1 | 7/2010 | Hawkes et al. |
| 2012/0228083 A1 | 9/2012 | Terzini |
| 2013/0310969 A1 | 11/2013 | Terzini et al. |
| 2014/0025545 A1 | 1/2014 | Carson et al. |
| 2014/0249666 A1 | 9/2014 | Radwallner et al. |
| 2014/0250829 A1 | 9/2014 | Terzini |
| 2017/0336780 A1 | 11/2017 | Wise et al. |
| 2018/0319592 A1 | 11/2018 | Yamashita |
| 2019/0371446 A1 | 12/2019 | Wollschleger |

OTHER PUBLICATIONS

Notice of Allowance dated Jan. 22, 2020, issued in U.S. Appl. No. 15/472,129, 15 pages.
Notice of Allowance dated Oct. 18, 2023, issued in U.S. Appl. No. 17/827,389, 11 pages.
Notice of Allowance dated Sep. 18, 2023, issued in U.S. Appl. No. 17/827,389, 13 pages.
Non-Final Office Action dated Jun. 23, 2023 issued in U.S. Appl. No. 17/827,389, 12 pages.
Notice of Allowance dated Feb. 3, 2022, issued in U.S. Appl. No. 16/856,157, 15 pages.
Non-Final Office Action dated Oct. 8, 2021, issued in U.S. Appl. No. 16/856,157, 10pages.

* cited by examiner

MODULAR PRODUCT DISPENSING AND VERIFICATION SYSTEM AND METHOD

CROSS-REFERENCES TO RELATED APPLICATIONS

This application is a continuation of U.S. patent application Ser. No. 17/827,389, filed May 27, 2022, entitled "Modular Product Dispensing and Verification System and Method, which is a continuation of U.S. patent application Ser. No. 16/856,157, filed Apr. 23, 2020, entitled "Modular Product Dispensing and Verification System and Method, which is a continuation of U.S. patent application Ser. No. 15/472,129, filed Mar. 28, 2017, entitled "Modular Product Dispensing Verification System and Method", now U.S. Pat. No. 10,669,098, and claims priority under 35 U.S.C. 119(e) and 37 C.F.R. 1.78(a)(4) based upon U.S. Provisional Application, Ser. No. 62/314,115, entitled "MODULAR PRODUCT DISPENSING AND VERIFICATION SYSTEM," filed Mar. 28, 2016, each of the forgoing applications is incorporated herein by reference in its entirety.

FIELD

The present disclosure generally relates to product dispensing and verification systems. More particularly, it concerns a modular system and method for dispensing products from an automated or manual dispensing station and transfer of the dispensed products to another automated or manual dispensing station for accumulating additional dispensed products, or transfer of the dispensed products directly to a verification station.

BACKGROUND

Product dispensing and verification systems, such as pharmacy dispensing systems, dispense a variety of prescription and non-prescription products from a stored inventory based on patient-specific orders. The various components of a patient order are generally accumulated in an open transport carrier such as a tote, and the contents are ultimately emptied into a labeled package for delivery to the patient. Fully automated systems are available that use robots to pick the products based on instructions from a computer control system. Such fully automated systems generally verify the accuracy of each dispensed item, its label, as well as the identity of the accumulated items by scanning sensors that are located on the robots, at each station where a product is added to a tote, and immediately prior to packaging. The sensors communicate with the control system to shunt totes with dispensing errors to a rejection station.

Fully automated dispensing systems can handle thousands of prescriptions per day, and are generally used by high volume pharmacies. However, they are not cost-efficient for use by smaller mail order, central-fill, or specialty pharmacies that process fewer than about 1500 prescriptions per day.

Previous attempts to semi-automate smaller pharmacies have employed robotic product dispensing units or dispensing robots and a computer software control system to perform some functions, such as order entry, automated tablet counting, and unit-of-use or pre-pack dispensing, while manually performing other dispensing functions such as manual counting, pharmacist verification, packaging and sorting. In such systems, products dispensed automatically by a dispensing robot are deposited into a tote, and the tote is placed on a transporting conveyor. The conveyor has a sequential, "racetrack" type configuration and includes a variety of additional stations positioned around the perimeter. These stations may include one or more stations for "countable" items that are manually dispensed by counting, stations for pre-counted items in "unit-of-use" packages or containers provided by a manufacturer or repackager, a verification station and a packaging station. Each station on the conveyor track forms a stop, at which the totes accumulate to await their turn for performance of the station function. If a particular tote does not require the item/function provided at the stop, an operator must intervene, such as by lifting the tote over the stop and placing it in a position on the conveyor past the station so that it can proceed to the next stations.

Such sequential, multi-station systems lack the ability to bypass one or more stations or stops. For example, they are unable to shunt single component orders directly from a robot dispensing unit to a verification station to bypass all of the manual dispensing stations in the system. The throughput speed of such semi-automated systems is limited by the need for each tote to stop at every station, and for each tote to be handled by an operator, either to dispense a product or to perform a function such as packaging, or to manually shift the tote past the station. Thus, these systems require the operations personnel and pharmacists to move around the pharmacy to fill patient orders. Such systems also require a substantial amount of floor space which is not always available in smaller pharmacies. In addition, they are not easily reconfigured to accommodate the addition or elimination of stations.

Thus, there is a need for an improved product dispensing system that can integrate computer-controlled robotic dispensing with traditional manual dispensing, verification and packaging functions and routing of totes, that can bring the orders to the personnel to allow them to be more efficient, that can mix and match various combinations of order processing stations so that all volume requirement needs are covered, that can easily accommodate addition or removal of stations depending on throughput requirements, and that can be configured and easily reconfigured, if necessary, to fit within the footprint of an existing pharmacy.

SUMMARY

The present disclosure provides a greatly improved modular system and method for dispensing a variety of products, such as pharmaceuticals, patient care items, and supplies, either in units of use, unit-dose packages, or counted into containers. The system provides for product dispensing using a combination of automated and manual dispensing stations, application of labels, accumulation of the dispensed products into a customer order, and verification of the contents of each order prior to packing out. The system is modular and scalable to enable it to be easily configured according to the available space as well and to facilitate addition or deletion of stations or substitution of automated stations for manual stations and vice versa. It also provides an efficient workflow with increased throughput that allows a completed order to proceed directly from any dispensing station to verification and customer distribution without the need for such completed orders to wait in line at additional dispensing stations before proceeding to verification.

The system includes a primary or central transporting conveyor assembly configured to form a central spine, commencing with one or more induction stations and followed by a plurality of processing stations for dispensing, product verification and packaging. Multiple processing stations of a type are arranged in pairs, each one of a pair arranged on a side of the conveyor. Optionally, both cold chain and ambient packaging stations may be provided. One or more sortation, and/or shipping and manifest stations are provided for removal of the dispensed products. The system also includes a control system for coordinating and controlling operation of the product dispensing system. In one aspect, the system may include one or more secondary transporting conveyor assemblies, such as a robot conveyor assembly. Items dispensed by the robot conveyor assembly are manually delivered to the central conveyor assembly.

The central conveyor assembly includes a four tier stack of conveyors, with crossover conveyors at each pair of manual dispensing stations. A package takeaway conveyor is connected with the central conveyor. Each conveyor tier includes a lane divider enabling two totes to travel side-by-side on the tier for access by a respective station of each station pair. Each station includes a tote stop structure, which automatically halts travel of a line of totes on the conveyor when the first tote in the line reaches the station. Totes are removed from the conveyor tiers for station processing such as document induction, product dispensing, verification, packaging, and sortation/manifest/shipping, and they are either replaced on the same conveyor tier at a position past the stop to enable continuation to the next station on the tier or they are placed on a different conveyor tier for routing to a different station. The package takeaway conveyor transfers packages from the packaging station or stations to the sortation and/or shipping manifest station. At this station, the packages may be transferred to another carrier such as a utility cart, depending on the final destination.

A first tier of the central conveyor transports empty totes from the packaging stations to the document induction workstation(s), where a routing and dispensing itinerary is placed in the tote. From the document induction station(s) totes are delivered manually or via a robot conveyor to the robot product dispensing station(s), or to the third or fourth conveyor tier for transport to the manual dispensing stations. From the robot dispensing stations totes may be manually deposited on the third or fourth tier for transport to the manual dispensing stations, or the totes may be deposited on the second tier for transport to the product verification station(s). From the manual dispensing stations the second tier transports totes to the product verification station(s). From the pharmacist verification station(s), totes are deposited onto the third tier for transport to the cold chain packaging station(s), or they may be deposited onto the second tier for transport to the ambient packaging station(s).

The manual dispensing stations may or may not dispense identical products. They also may or may not dispense products in identical packages or containers, such as unit-of-use products or countable products. Thus, any manual station can dispense unit-of-use products or countable products. Pairs of crossover conveyors are positioned between the pairs of manual dispensing stations to enable dispensing of a product at one of a pair of dispensing stations, followed by dispensing of a product at one of the pair of dispensing stations on the opposite side of the central conveyor.

The document induction workstations each include a support structure, such as a table, supporting a computer terminal with a user interface, a printer, and document staging structure. The computer terminal includes a processor that is operable to provide access to a database where patient orders may be accessed. The printer is operable to print a routing and dispensing itinerary corresponding to a patient order. The document(s) are deposited in the tote and the tote is routed in accordance with the itinerary. The tote may be initially routed for delivery to an automatic or robotic dispensing unit, or it may be routed for delivery to a manual dispensing station. The tote may be manually delivered to a dispensing robot designated on the dispensing itinerary. It may be manually delivered from the dispensing robot to a conveyor tier for routing to additional dispensing robots, to manual dispensing units, or directly to a verification unit.

In another aspect, the totes are initially delivered to a dispensing robot via a robot conveyor assembly, which may have a 4 tier configuration similar to the central conveyor assembly. Tier 1 transports totes from the document induction workstation to a first dispensing robot. Tier 2 transports totes from the document induction workstation to a second dispensing robot. Tier 3 transports totes with completed dispensing itineraries back to the induction workstation. Tier 4 transports totes for orders requiring additional items back to the induction workstation.

At least one conveyor tier adjacent each pair of manual dispensing station includes a stop structure. Each manual dispensing station includes a computer terminal, barcode scanner, and labeler. Each dispensing station also includes a stored quantity of one or more products. Dispensing robots and manual dispensing stations capable of dispensing countable items, such as pills, also include a device and supplies of containers for retaining the items after counting. At least one conveyor tier adjacent each pair of packaging stations also includes a stop. Packaging stations also include a printer for printing a delivery manifest for the products. At least one conveyor tier adjacent the sortation and manifest station also includes a stop. The sortation and manifest station also includes utility carts and boxes or totes for delivery of the dispensed products to their final destination or storage.

Storage structures such as high density shelving units are positioned adjacent each manual dispensing and packaging workstation for providing supplies of products, packaging and storage materials. Refrigeration units are positioned adjacent manual dispensing stations designated for dispensing products requiring refrigeration and packaging stations designated for packaging cold chain products.

The control system is a computer control system and includes a computer or processor, having an input/output section, central processing unit (CPU) and memory section. The computer may be connected to a network for receipt of patient order, inventory, verification and any other information necessary for operation of the product dispensing and verification system.

Another embodiment adapted for increased throughput employs the system as a first module dedicated to unit-of-use items that may be refrigerated or kept at ambient temperature. This embodiment includes a second module dedicated to countable products at ambient temperature. The second module includes a primary or central transporting conveyor assembly configured to form a central spine with a manual countable workstation at one end and a plurality of processing stations, multiples of which are arranged by type in pairs, each one of a pair positioned on one side of the conveyor. The central conveyor assembly includes a three tier stack of conveyors with stops at the stations. The third tier forms a transfer spur at the product verification stations for transfer of totes requiring additional unit-of-use products and/or refrigeration to the first module, leaving the central conveyor with two tiers between the spur and the first end. A portion of this first end is surmounted by a staging platform for totes containing medications dispensed by a bank of robots positioned at the first end of the conveyor. A package takeaway conveyor is connected with the central conveyor in the vicinity of the packaging stations for transporting packages from the packaging station(s) to a shipping and manifest station shared with the first module.

A first tier of the central conveyor transports empty totes from the single container and multiple container packaging stations to the first end of the conveyor. Induction printers generate a routing and dispensing itinerary, that is deposited into an empty tote or a partially filled tote obtained from the robot dispensing staging area. Empty or partially filled totes may be manually delivered to the manual countable workstation. Once a tote contains a completed dispensed order it is deposited on the second tier conveyor for transport to the pharmacist verification stations. From the verification station(s), totes are deposited onto the second tier for transport to the multiple container packaging stations or onto the third tier conveyor for transport to the single container packaging stations, or onto the transfer spur for transfer to the induction station of the first module. In a transfer, the contents of the tote are emptied into a new tote for use in the first module and the original tote is deposited on a short tote return tier positioned below the transfer spur. Totes arriving at the end of the tote return tier are manually deposited onto the second tier tote return for transport to the first end of the central conveyor.

Another embodiment adapted for lower throughput includes a central transporting conveyor assembly having a ring configuration, with a plurality of processing stations arranged around the perimeter. The central conveyor includes a two tier stack of conveyors with a pair of lanes and stops at the stations on the upper, second tier and a freely circulating lower, first tier. The second tier of the conveyor transports empty totes from the packaging stations by the outer lane for transport to the first manual dispensing station, and by the inner lane for transport to the second manual dispensing station. A printer at the first dispensing station produces a routing and dispensing itinerary which is placed in an empty tote with items dispensed at the first station. From the first dispensing station, totes with completed orders are deposited on the first conveyor tier for transport to the verification station(s) or on the outer lane of the second conveyor for transport to the second verification station for dispensing of additional items. The second dispensing station retrieves totes from both lanes and deposits products according to the dispensing itinerary. The completed orders are deposited onto the first tier for transport to the verification station. From the verification station, totes are deposited into the second tier outer lane for transport to the packaging stations. From the packaging stations, empty totes are deposited on both the outer and inner lanes of the second tier for delivery to the respective first and second dispensing stations.

Various objects, features and advantages of this disclosure will become apparent from the detailed description which follows. The summary, taken in conjunction with the accompanying drawings, depicts illustrations and examples of certain embodiments of this disclosure.

DETAILED DESCRIPTION

The subject matter of select embodiments of the invention is described in sufficient detail to enable those skilled in the art to practice the invention. However, the disclosed embodiments are merely exemplary of the system and method, which may be embodied in various and alternative forms. The figures are not necessarily to scale and some features may be exaggerated or minimized to show details of particular components. Therefore, the specific structural and functional details disclosed are not to be interpreted as limiting, but merely as a representative basis for the claims and for teaching one skilled in the art to variously employ the modular product dispensing and verification system.

A modular product dispensing and verification system 1 in accordance with the disclosure is illustrated in FIGS. 1-7. The system 1 includes a primary or central transporting conveyor assembly 2, having one or more document induction stations 4 positioned adjacent one end of the assembly 2 and a variety of order processing stations positioned in spaced relation along the sides and adjacent the other end of the assembly. The order processing stations may be configured to provide all fulfillment requirements of an order from induction to shipping in an efficient manner. One or more robotic dispensing stations 6 may be positioned in spaced relation to the conveyor assembly 2 and the induction station(s) 4.

Figure 2:
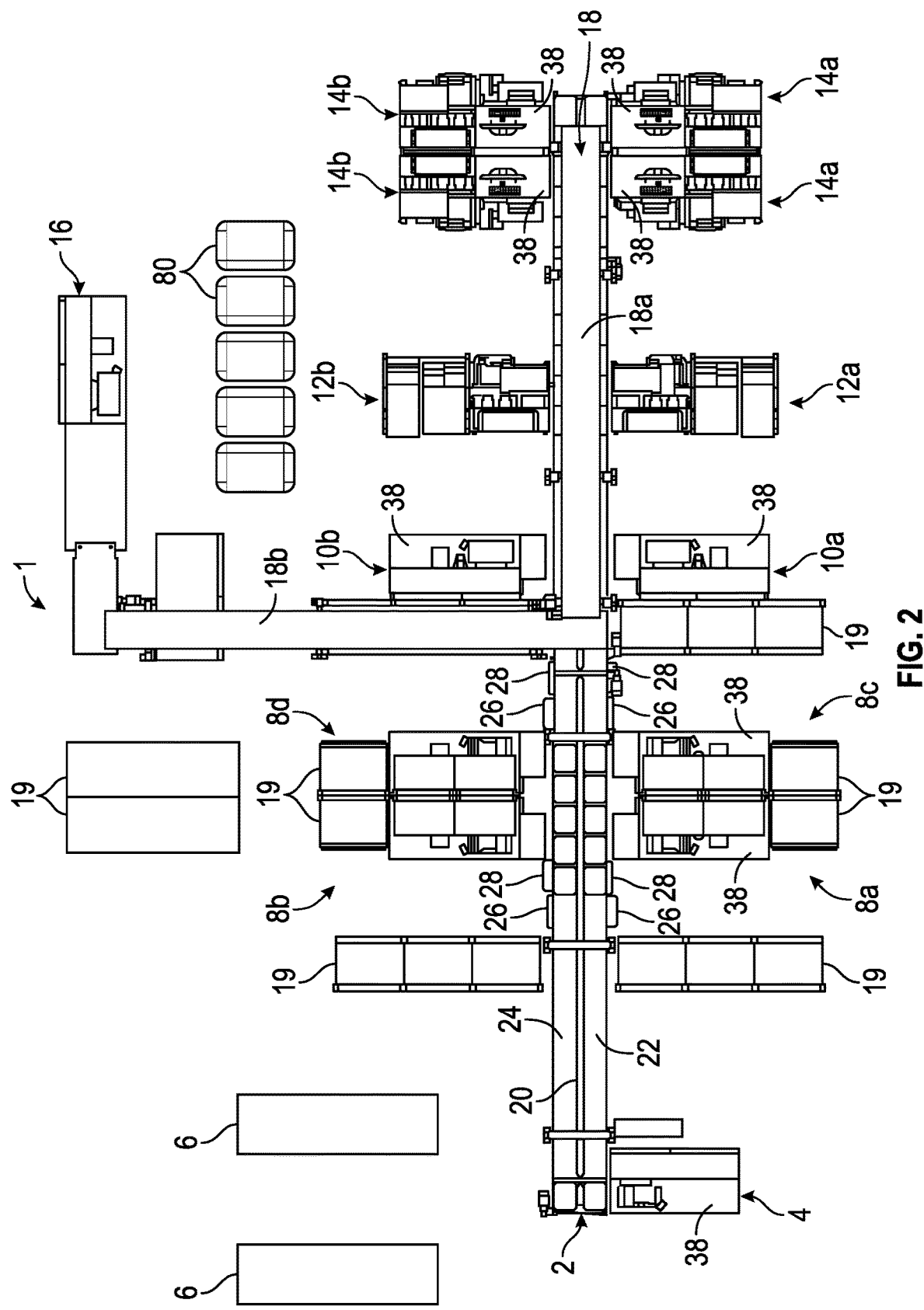
FIG. 2 is a top plan view of the system shown in FIG. 1.
Figure 7:
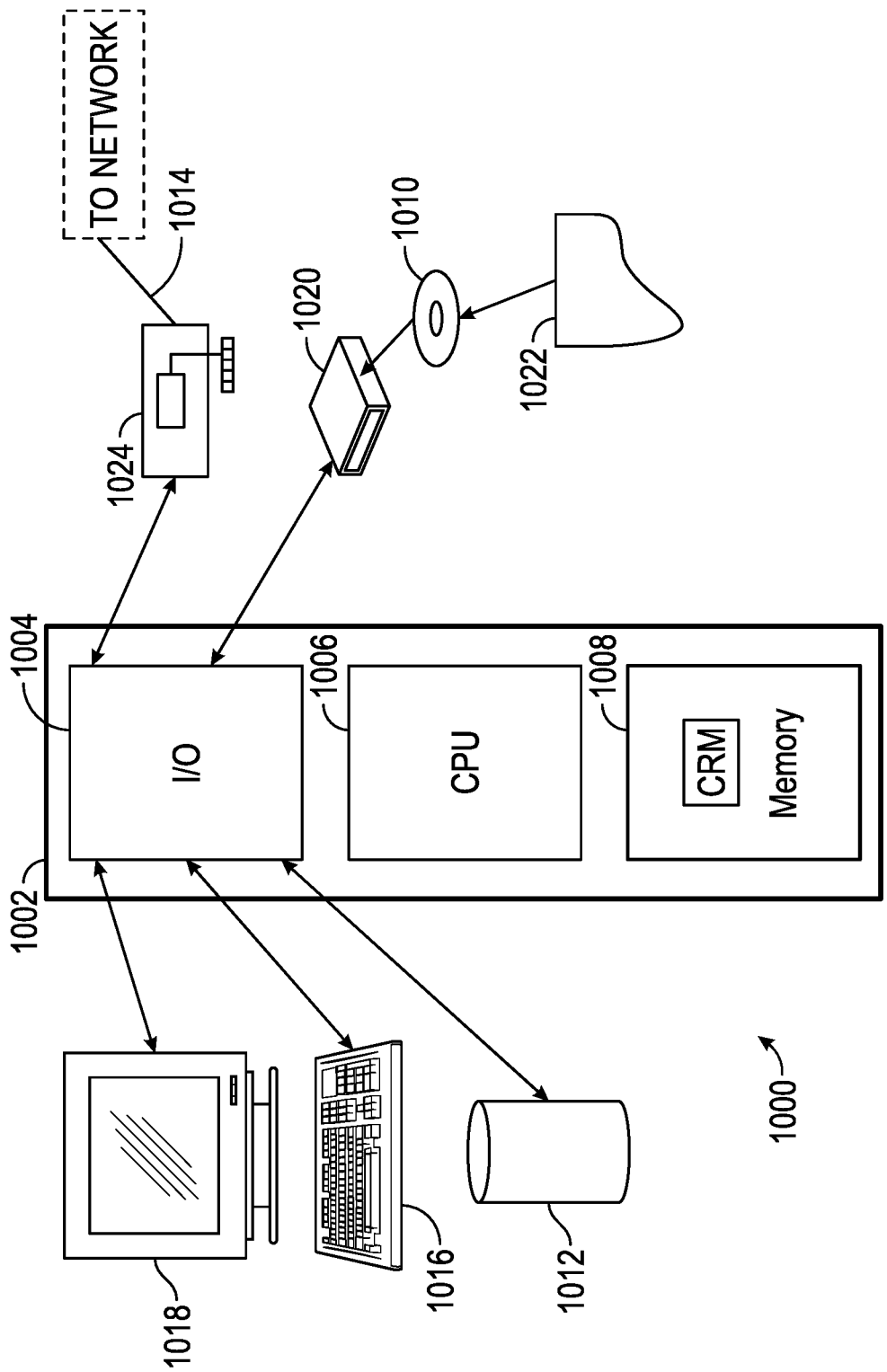
FIG. 7 is a diagrammatic representation of a control system of the modular product dispensing and verification system.
Figure 8:
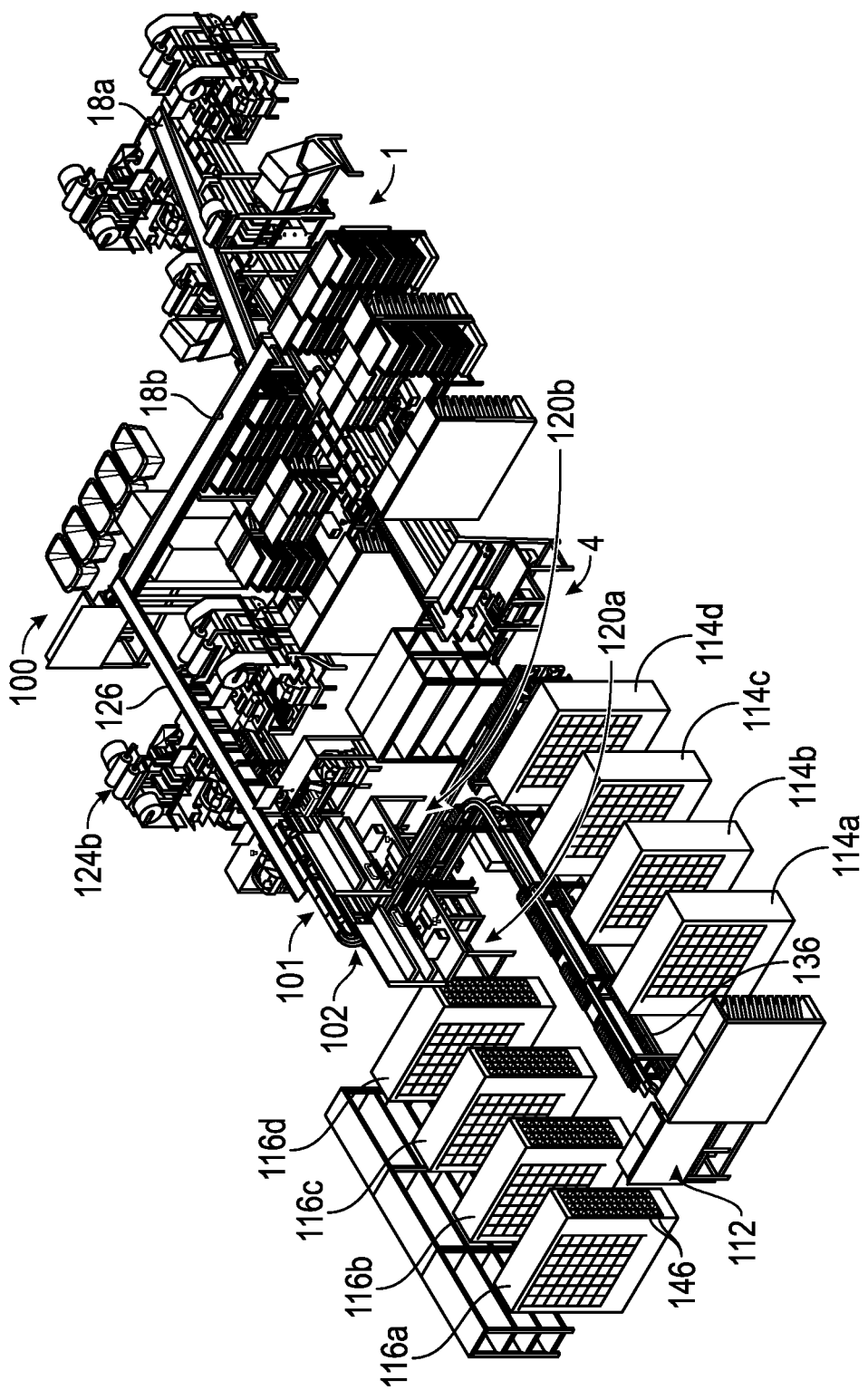
FIG. 8 is a perspective view of an embodiment of a modular product dispensing and verification system adapted for greater product throughput.
Figure 9:
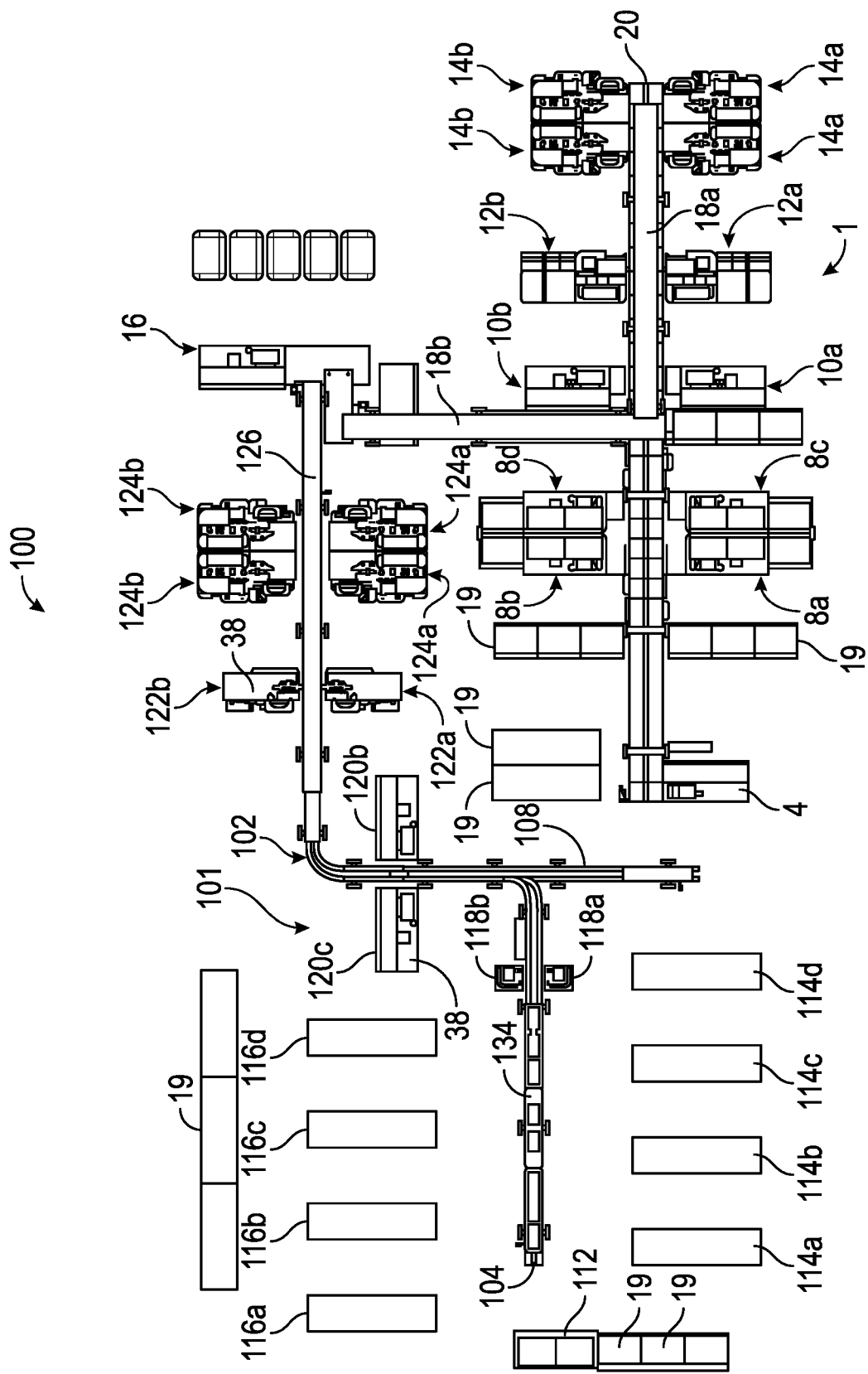
FIG. 9 is a top plan view of the system shown in FIG. 8

As best shown in FIG. 2, the central conveyor 2 forms an elongate, central spine with pairs of dispensing or fill stations 8a, 8b and 8c, 8d, a pair of pharmacist product verification stations 10a and 10b, a pair of cold chain packaging stations 12a and 12b, and a pair of ambient packaging stations 14a and 14b, disposed in spaced relation adjacent the sides of the conveyor. A station 16 for sortation, manifest and shipping is connected in lateral spaced relation to the central conveyor 2 by a package takeaway conveyor 18. It is foreseen that the system 1 may be configured to include one or a plurality of each type of station as needed. One or more stations may also be omitted if not required. High density storage units 19 for storing products 21 and packaging materials are positioned in adjacent or conveniently spaced relation to the stations. A control system 1000 coordinates and controls operation of the system 1 (FIG. 7).

Figure 3:
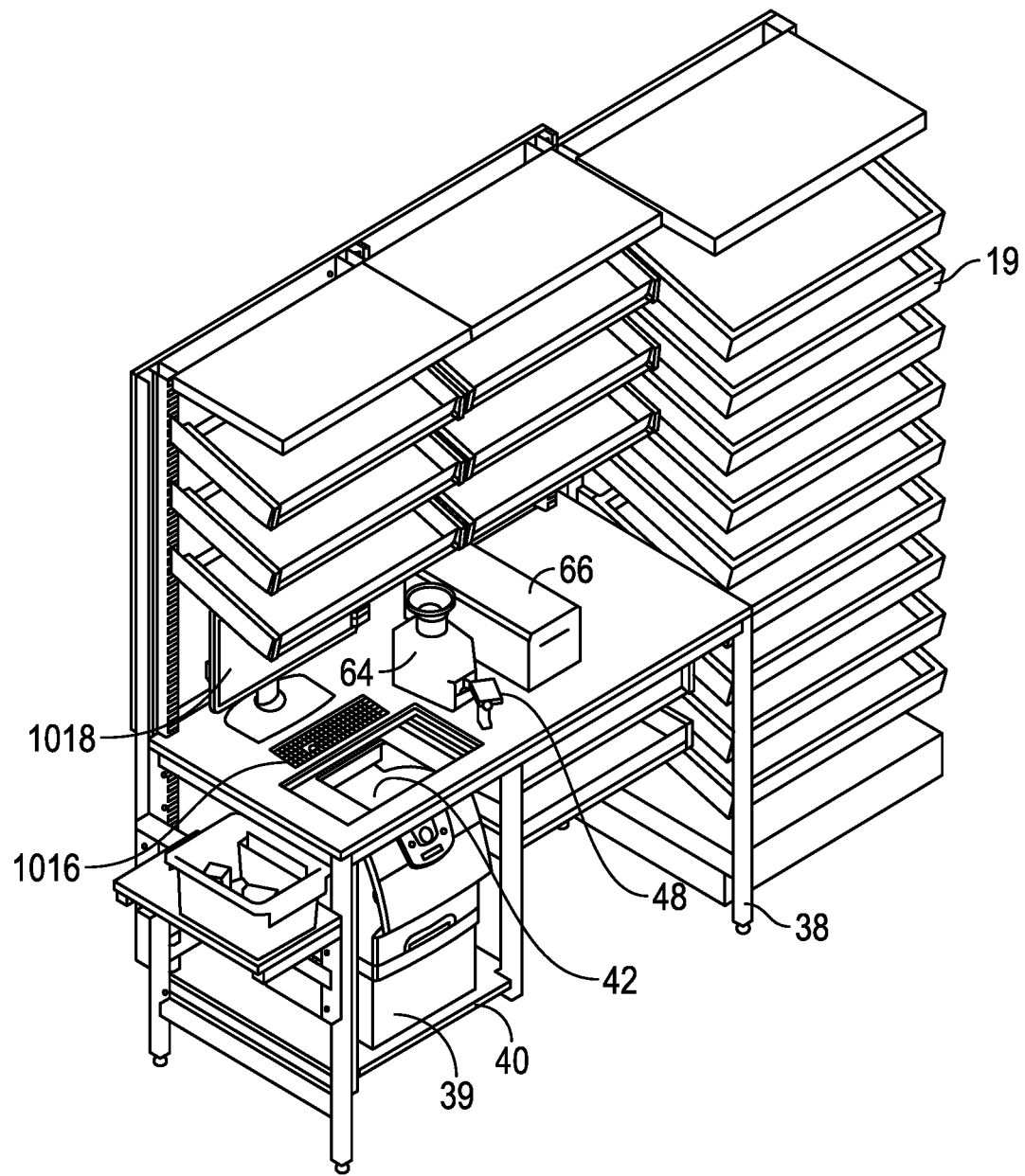
FIG. 3 is an enlarged perspective view of an exemplary workstation shown in FIG. 1.
Figure 4:
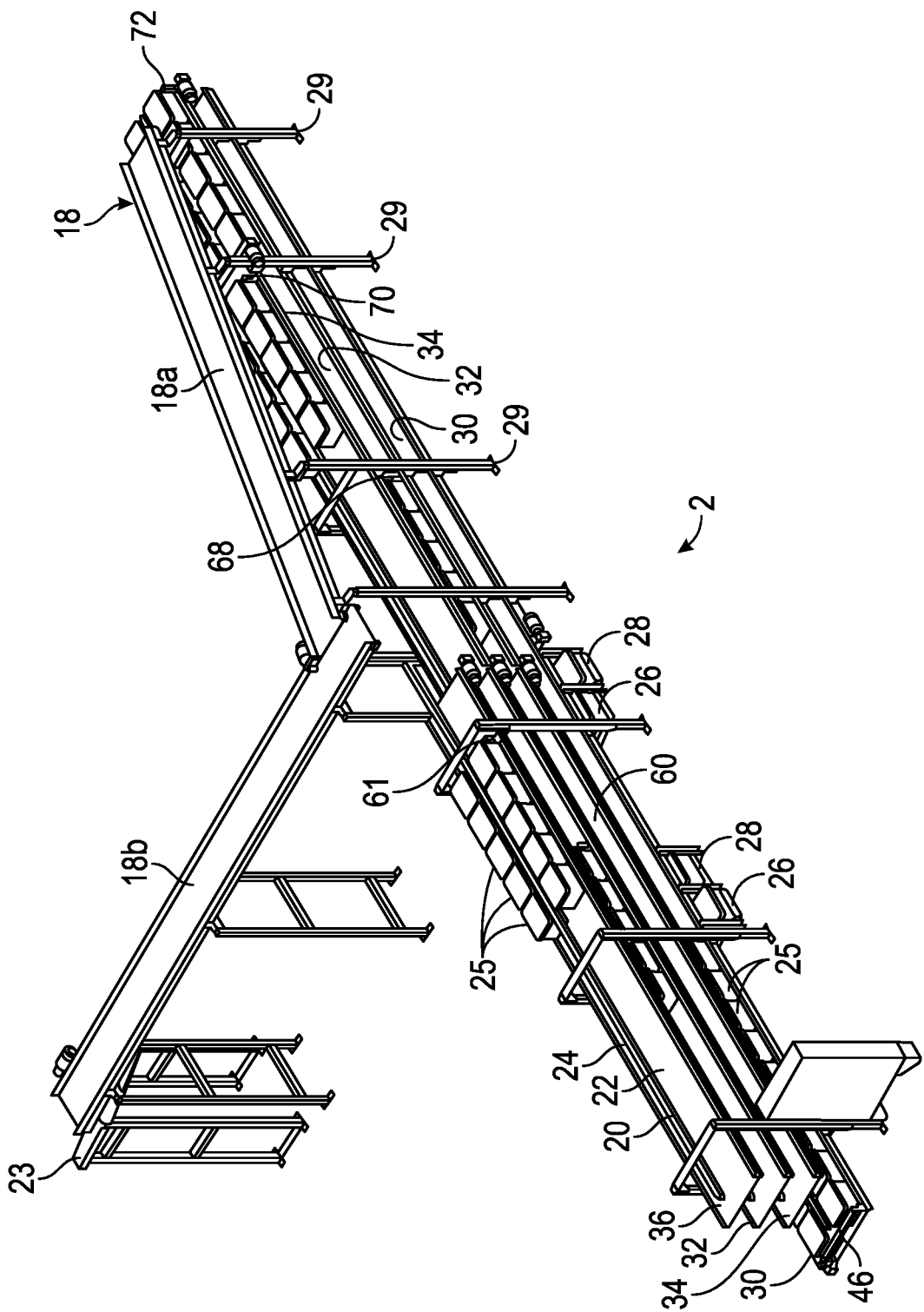
FIG. 4 is an enlarged perspective view of the central and package takeaway conveyor assemblies shown in FIG. 1.
Figure 5:
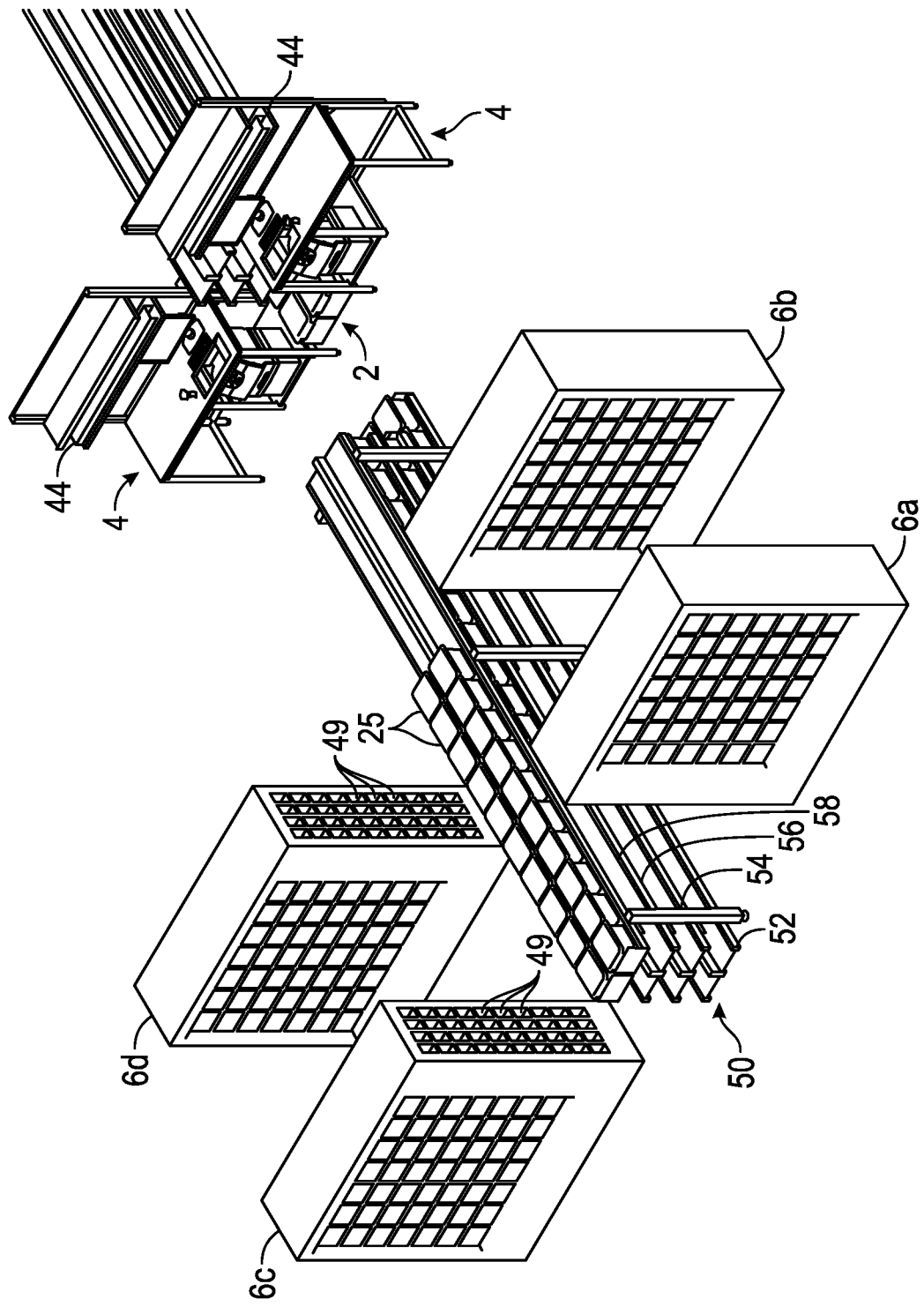
FIG. 5 is an enlarged partial perspective view of an embodiment including 4 robot dispensing units and a robot conveyor.
Figure 6:
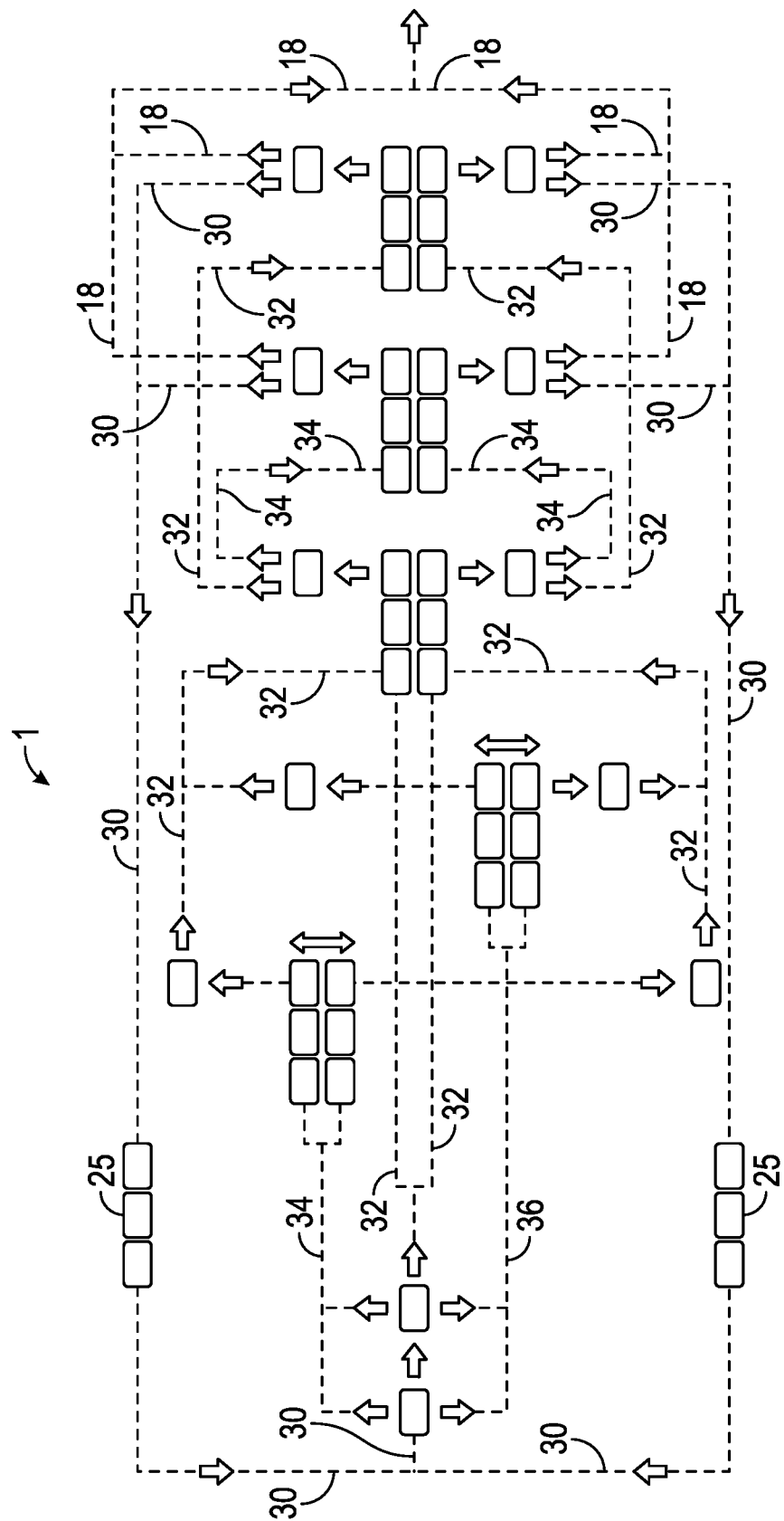
FIG. 6 is a flow diagram showing the sequence of movements and actions in accordance with the system shown in FIG. 1.

As best shown in FIG. 4, the primary or central transporting conveyor assembly 2 includes multiple levels or tiers of vertically spaced-apart conveyors configured in a vertical stack. While belt-type conveyors are illustrated, roller-type conveyors could also be employed. The surface of each conveyor is equipped with an upstanding, longitudinally oriented lane divider 20 that separates the upper surface of the respective conveyor lengthwise into a pair of first and second lanes 22 and 24. The lanes 22 and 24 are sized to accommodate carriers such as totes 25 for travel on the conveyor surface in side-by-side relation on a respective tier. The central conveyor assembly 2 also includes a pair of tote transfer or crossover conveyors 26 and 28, (FIGS. 2-4), positioned transversely below the first tier 30 of the central conveyor 2 and between the members of each pair of manual dispensing stations 8a, 8b and 8c, 8d, which pair members are positioned on opposite sides of the central conveyor 2. The crossover conveyors 26 and 28 are preferably gravity incline/decline roller conveyors that are configured to extend downwardly at an angle between the respective manual dispensing workstations 8a and 8c on one side of the central conveyor to the other member of the pair of dispensing workstation 8b or 8d on the opposite side of the conveyor. This enables workers at a manual dispensing station 8a or 8c on one side of the central conveyor 2 to slide a tote below the central conveyor 2 to the other member of the station pair 8b or 8d for dispensing additional items into the tote (and vice versa) while the tote remains at the same manual dispensing station 8a, 8b or 8c, 8d.

The central conveyor assembly 2 (FIGS. 1 and 4) includes four conveyor tiers mounted in a framework or frame 29. While the illustrated framework is constructed of multitier single-support type floor-mounted frames or stands, the conveyor assembly 2 may be supported in any suitable manner, including by overhead framework. The tier 1 or tote return conveyor tier 30 is positioned at the lowermost or bottom level of the conveyor stack. The tier 1 conveyor 30 transports returning empty totes from the cold chain packaging stations 10a, 10b and ambient packaging stations 14a, 14b to the document induction station(s) 4 for reuse. The tier 2 conveyor tier 32 is mounted in spaced relation above the tier 1 conveyor. Because the robot dispensing units 6 are positioned in spaced relation to the central conveyor 2, totes are manually transferred from the robot dispensers 6 onto the tier 2 conveyor 32, which transports the totes directly to the pharmacist verification stations 10a, 10b, and from a verification station 10a or 10b to the ambient packaging stations 14a, 14b. Tier 2 may also be used to transfer totes from a manual dispensing station pair 8a, 8b or 8c, 8d to the pharmacist verification stations 10a, 10b and to transfer totes from a pharmacist verification station 10a or 10b to an ambient packaging station 14a or 14b. The tier 3 conveyor 34 is positioned in spaced relation above the tier 2 conveyor 32, and transports totes from the document induction station 4 to the manual dispensing stations 8c, 8d for dispensing. Tier 3 may also be used to transport totes from the pharmacist verification stations 10a, 10b to the cold chain packaging stations 12a and 12b. The tier 4 conveyor 36, is positioned in spaced relation above the tier 3 conveyor 34, and transports totes from the document induction stations 4, as well as totes manually transferred from the robotic dispensing units 6, to the manual dispensing station pair 8a and 8b.

The package takeaway conveyor 18 has a generally L-shaped configuration including a first leg 18a and a second leg 18b. The first leg 18a commences at the ambient packaging stations 14a, 14b, and extends upwardly at an angle over the third conveyor tier 34 but within reachable distance of the operators of the cold-chain packaging stations 12a and 12b and continues upwardly above the verification stations 10a and 10b to the second leg 18b. The conveyor takeaway second leg 18b has a generally horizontal orientation, with one end positioned slightly below the end of the first leg 18a, so that products drop off the end of the first leg 18a and onto the second leg 18b. The second leg 18b extends laterally away from the central conveyor assembly 2 to the manifest and shipping station 16, and includes a chute 23 at the outboard end to facilitate removal of the packaged orders by the station operator and routing of the packages to their final destinations (FIG. 4). After packaging, the operators of the packaging stations 12a, 12b and 14a, 14b return the empty totes to the document induction station 4 via the tier 1 tote return conveyor 30.

The document induction workstation 4 (FIGS. 1-2) is positioned adjacent one end of the central conveyor 2. An exemplary workstation is illustrated in FIG. 3 to include a work table 38 for supporting computer user interface components such as a keyboard 1016 and display unit 1018 that enable a workstation operator to access a network where orders, such as patient orders are stored. The user interface also includes a printer device 39 mounted on a printer deck 40 below the work table 38. A window structure 42 is positioned in the workstation above the printer deck 40, so that the operator can verify that all pages of an order have printed before removing a printed document or document set 41 and placing it in a staging structure 44 (FIG. 1) used to organize the document sets in discrete locations. The document or document set 41 corresponds to an order, such as a patient prescription order, and includes a routing and dispensing itinerary or "traveler" that accompanies medications dispensed in accordance with the patient order throughout the dispensing and verification system 1. It is foreseen that the document induction workstation 4 may also include a scanning device 48, such as a barcode scanner, which may be fixed or handheld. Each lane of the conveyor first tier 30 includes a stop structure 46 at the end adjacent the document induction station 4, causing empty totes 25 to accumulate for use by the station operator.

An induction workstation operator removes an empty tote 25 at the induction conveyor stop 46 and deposits it on the induction workstation table 38. The display monitor 1018 prompts the operator to select a patient order dispensing itinerary from the document staging structure 44, deposit it into the empty tote 25, and then deposit the tote 25 in a designated lane 22 or 24 of a designated conveyor tier for delivery of the tote and itinerary to a next station in accordance with the dispensing itinerary.

In another aspect, the document induction workstation printer 39 is operable to print a document set having a unique bar code or patient order identification (POID) on each document associated with a patient order. Each tote 25 is provided with a unique bar code, or tote identification (TID). The document induction workstation operator scans the patient order ID and the tote ID on an empty tote delivered to the station via conveyor tier 1. These two scanned bar codes, POID and TID, are associated via the computer software. Once this association between a patient order ID and a tote ID has been established, scanning the tote bar code (TID) at a system workstation operates to populate the display unit 2018 at the workstation with the patient order and workstation itinerary, obviating the need for a paper order itinerary.

Figure 1:
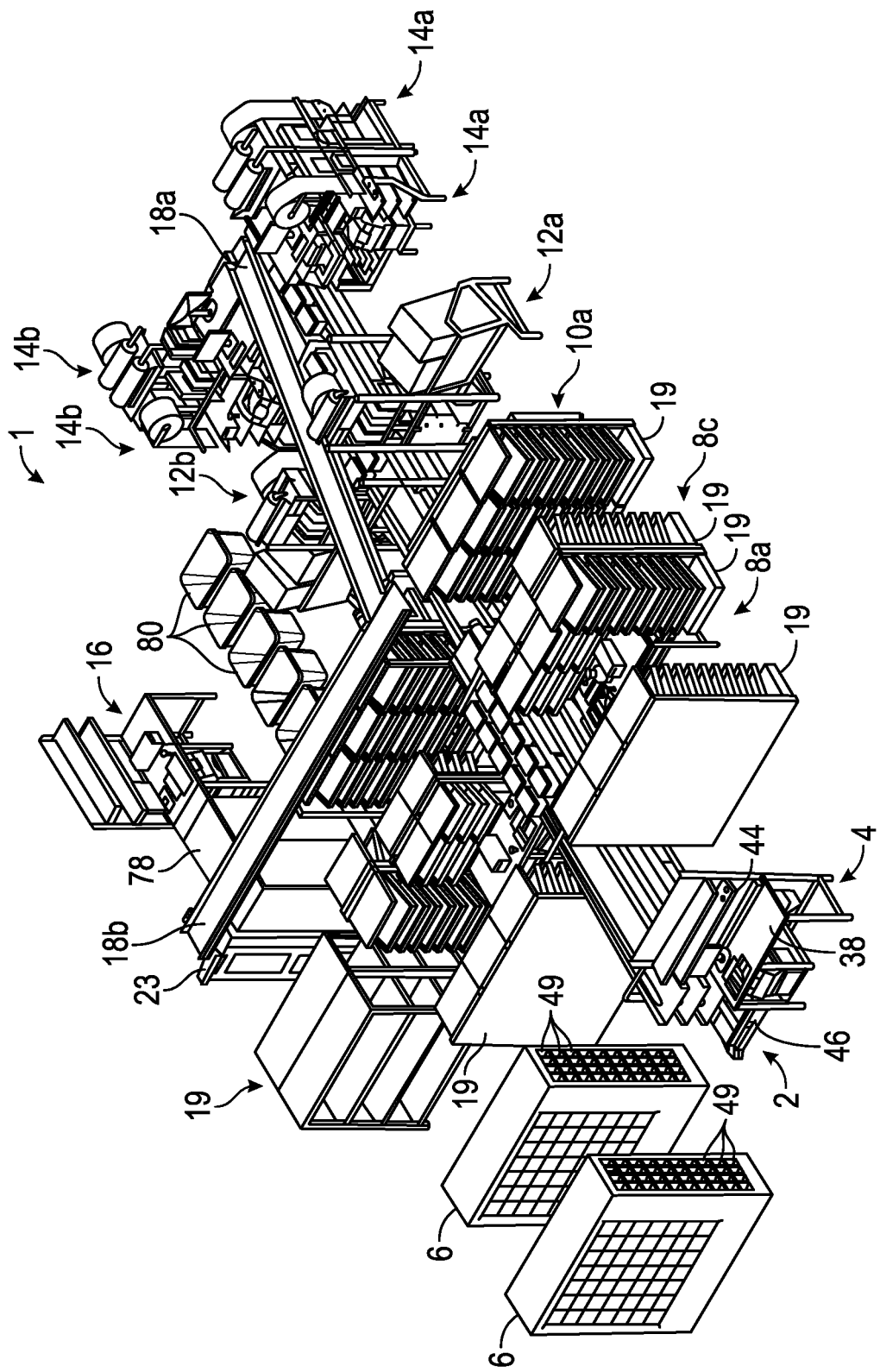
FIG. 1 is a perspective view of a modular product dispensing and verification system in accordance with the disclosure

The dispensing itinerary 41 may call for initial routing of the tote the tote 25 to one or more of the robotic dispensing station 6a or 6b (FIGS. 1 and 2). While robotic dispensing equipment is capable of dispensing both countable and unit-of-use or prepackaged items, they are most effective at increasing system throughput when used to dispense the most frequently ordered countable items. The control system 1000 directs one or more dispensing robot(s) to dispense one or more medications in accordance with the routing and dispensing itinerary 41. An operator obtains a tote from the tier 1 conveyor 30 and an itinerary 41 from the document induction station 4 and carries them the robot dispensers (FIG. 6), where one or more respective robots has dispensed countable items into a container, applied a label, and deposited the containers into an order accumulation area 49 connected to the respective robot dispenser. The operator retrieves the labeled container(s), scans the labels and places them into the tote 25 with the dispensing itinerary 41 and manually routes the tote by depositing it on the tier 3 conveyor, 34 or the tier 4 conveyor 36, for transport to the manual dispensing station pairs 8c, 8d or 8a, 8b, or deposits it on the tier 2 conveyor 32 for transport directly to the pharmacist verification station pair 10a, 10b.

In another aspect, the system 1 includes robots 6a, 6b, 6c, and 6d and a robot conveyor assembly 50, (FIG. 5) to transport totes 25 from the document induction station 4 to the robot dispensing stations 6a, 6b, 6c, and 6d. The robot conveyor assembly 50 includes four tiers or levels of conveyors. A first robot conveyor tier 52 transports totes 25 with dispensing itineraries from the document induction workstation 4 to a first dispensing robot 6a. A second robot conveyor tier 54 transports totes from the document induction workstation 4 to a second dispensing robot 6b. A third robot conveyor tier 56 transports totes with completed robotic dispensing itineraries back to the induction workstation. The tote is then transferred to tier 2 of the central conveyor assembly 2 for transport to a pharmacist verification station 10. It is also foreseen that a robot crossover conveyor may be provided to transfer a tote from dispensing a robot positioned on one side of the conveyor assembly 50 to a dispensing robot positioned on the other side of the conveyor where an order requires additional items from a non-adjacent dispensing robot. A fourth robot conveyor tier 58 transports totes with robot-dispensed orders back to the induction workstation 4 for transfer to central conveyor tier 3 or tier 4 for transport to an appropriate manual dispensing station pair 8c, 8d or 8a, 8b for dispensing of additional products. Alternatively, if the order is complete and no additional medications are required, the induction workstation operator transfers totes to the tier 4 central conveyor 36 for transport directly to the verification station pair 10a, 10b.

The document induction station 4 may initially route a tote to a manual dispensing station pair 8a, 8b or 8c, 8d (FIG. 2). Each of the dispensing stations includes an array of high density storage units 19 for short-term storage of quantities of preselected medications. Each station may be configured to store a variety of different medications. It is also foreseen that frequently dispensed medications may be stocked at more than one dispensing station. In order to increase throughput, individual stations may also be configured to dispense one of either countable items such as pills, or unit-of-use or prepackaged items such as tubes, prepackaged multiple-unit containers, i.e., blister packs, and the like. One or more stations may also be designated for dispensing products that require refrigeration. Separate conveyor tiers are assigned to each dispensing station pair. For example, totes may be routed to manual dispensing station pair 8a, 8b for medications via the tier 3 conveyor 34, and to manual dispensing station pair 8c, 8d for medications via the tier 4 conveyor 36. Each conveyor lane 22, 24 in the tier 3 conveyor 34 includes a manual dispensing stop structure 60 adjacent manual dispensing station pair 8a, 8b, and each lane 22, 24 in the tier 4 conveyor 36 includes a manual dispensing stop structure 61 adjacent manual dispensing station pair 8c, 8d. (FIG. 4).

The manual dispensing workstations 8a, 8b, 8c, and 8d each include the elements previously described and shown in FIG. 3, including a work table 38 supporting a keyboard 1016 and display unit 1018, a printer 39, a scanning device 48, as well as product storage units 19, and a stored quantity of products 21 for dispensing. Manual dispensing stations that dispense countable items also include a counting device 64 of conventional construction, as well as a supply of containers and caps. The counting device is preferably a semi-automatic counting machine capable of counting pills, capsules, tablets and the like. The manual dispensing stations each also include a labeling device 66 for labeling containers of dispensed medications.

Operators of the manual dispensing workstations 8c and 8d each remove a tote 25 from a respective stop 61 in the adjacent lane 22 or 24 of the tier 4 conveyor 36. The operators of manual dispensing stations 8a and 8b each remove a tote 25 from a respective stop 60 in the adjacent lane 22 or 24 of the tier 3 conveyor 34. The operator then scans the document itinerary, which causes the computer display unit 1018 to display order information for the station.

If the manual dispensing station is designated for dispensing of unit-of-use products and the product to be dispensed is a pharmaceutical for human use, the display unit 1018 shows the specification of the unit-of-use product stock bottle or package to be dispensed along with a display of a product image (if available) so that the operator can obtain the correct product from the station storage unit 19. The display unit 1018 prompts the operator to scan the product stock bottle or package National Drug Code (NDC) product identifier and to actuate the labeler 64 to print the prescription label. If the wrong product is scanned, no label can be printed. After the prescription is dispensed and the label is printed and applied, the operator is prompted to scan the label, the control system 1000 verifies that it is the right label, and records the prescription as filled, along with the operator ID, date, and time of filling. The display unit 1018 then prompts the operator to place the product into the tote and to deposit the tote on either the tier 2 conveyor 32 for transport directly to the pharmacist verification station 10, or on the respective tote crossover conveyor 26 or 28 for transport to the other manual dispensing station of the station pair. These steps are repeated until manual dispensing of the order is completed.

If the manual dispensing station is designated for dispensing countable products, the display unit 1018 shows the specification of the of the countable product to be dispensed along with a display of the product image (if available) so that the operator can obtain the correct product from the station storage unit 19 along with a container and cap. The display unit 1018 prompts the operator to scan the stock bottle NDC product identifier and actuate the labeler 64. The operator then fills the container, scans and applies the container label and deposits the labeled container into the tote 25. Scanning the container operates to associate the container to the tote and records the prescription as filled, along with the operator ID, date, and time of filling. The display unit 1018 then prompts the operator to place the container into the tote and to deposit the tote on either the tier 2 conveyor 32 for transport to the pharmacist verification station 10, or on the respective tote crossover conveyor 26 or 28 for transport to the other manual dispensing station of the station pair. These steps are repeated until manual dispensing for the order is completed.

A tote containing a completed order and associated document itinerary 41 may be transferred to the pharmacist verification station pair 10a, 10b either directly from the robot dispensing stations 6a, 6b, 6c, 6d, or from a respective manual dispensing station pair 8am 8b or 8c, 8d via the tier 2 central conveyor 32. Each conveyor lane 22, 24 at the verification station pair 10a, 10b includes a stop structure 68. Each pharmacist verification station includes a display unit 1016 and keyboard 1018, and a scanning device 48, all as previously described.

Pharmacists at the verification workstations 10 and 10b each remove a tote 25 from the stop 68 in a respective adjacent lane 22 or 24 of the tier 2 conveyor 32. The pharmacist transfers the tote to the workstation 10, and scans the document itinerary barcode. This causes the computer display unit 1018 to display the order information. The pharmacist verifies each prescription in the tote, one by one. As the label on each item is scanned, the display unit 1018 shows details of the prescription and the reference drug image (if available). Once the pharmacist is satisfied that the item has been correctly dispensed, he or she indicates acceptance using a function key on the keyboard 1016 or touching a button on a touch screen display unit 1018. The pharmacist rejects any incorrectly dispensed prescription and enters reason(s) for rejection. When the pharmacist has accepted all items in the tote, the display unit prompts the pharmacist to deposit the tote onto the tier 2 conveyor 32 for transfer to the ambient packaging station pair 14a. 14b or to deposit the tote onto the tier 3 conveyor 34 for transfer to the cold-chain packaging statin pair 12a, 12b.

In another aspect, the tier 3 conveyor 34 also extends from the manual dispensing stations 8c, 8d, to the pharmacist verification stations 10a, 10b thereby enabling both manual dispensing station pairs 8a, 8b and 8c, 8d to transfer totes after dispensing to pharmacist verification stations 10a, 10b using the same tier 3 conveyor 34.

Each lane 22, 24 in the tier 3 conveyor 34 at the cold chain packaging station 12 includes a stop 70, and each lane in the tier 2 conveyor 32 at the ambient packaging station 14 also includes a stop 72. The totes 25 queue up at the respective packaging station stops 70 or 72 to await packaging of the products by an operator. Each packaging station 12 and 14 includes a worktable 38, document printer 39, on a printer deck 40, keyboard 1016, display unit 1018, scanner 48, and a labeler 64 as previously described. Cold chain packaging stations also include refrigeration units 78 for maintaining the cold temperature of the products.

The operators of cold chain packaging stations 12a and 12b each remove a tote 25 from a respective stop 70 in the adjacent lane 22 or 24 of the tier 3 conveyor 34. The operators of ambient packaging stations 14a and 14b each remove a tote 25 from a respective stop 72 in the adjacent lane 22 or 24 of the tier 2 conveyor 32. The operator deposits the tote onto the respective packaging workstation 12a or 12b or 14a or 14b and then scans the document itinerary barcode which causes the computer display unit 1018 to display order information for the station. This causes the computer display unit 1018 to display appropriate order information. The packer collects the contents of the tote and scans each of the prescription labels.

Once the control system 1000 has verified the order status as correct for packaging, it actuates the document printer 39 to print a set of patient-specific documents or literature pack, which includes instructions for use of each medication or product, drug literature, and optional marketing materials and/or coupons. In another aspect, the patient documents may be printed at the document induction station 4 or dispensing stations 8a, 8b, 8c, 8d and deposited in the tote along with the routing and dispensing itinerary. The control system 1000 then checks that the scanned items all match the items indicated on the order, and actuates the label printer 64 to print a label for a packaging unit, such as a bag or box. If the control system 1000 determines a mismatch, that is, a scanned item that does not belong in the order, or if a prescription status is incorrect, the display unit 1018 displays an error message including instructions to the station operator to discard any printed documents and requiring a supervisor to enter a password to clear the error. If the error is attributable to incorrect scanning, the station operator re-processes the items from the tote. If the error is attributable to missing/additional/incorrect items or incorrect prescription status, the station operator hands off the tote 25 to an exceptions worker and proceeds with the next tote.

Once an order has been successfully checked and a package label printed, the packer is prompted to apply the printed label to a new empty package or bag, place the items into the package, and scan the barcode on the label. The control system verifies that the barcode on the label matches the order, and the display monitor prompts the packer to seal the package and deposit it onto the package takeaway conveyor 18. The station operator then deposits the empty tote onto tier 1 of the conveyor 30 for return to the document induction station 4.

Packages are delivered to the sorting, manifest, and shipping station 16 via the package takeaway conveyor 18a, 18b. The sortation station 16 is configured substantially as previously described to include a worktable 38, document printer 39, keyboard 1016, a display unit 1018, and a labeler 64 as previously described. The package labels include barcodes, which also include human readable numbers indicating primary and final destinations. Operators remove the packages from the conveyor 18 and sort them into a plurality of utility carts 80. An operator removes carts as they fill, and sorts the contents into shipping containers such as crates or boxes for shipping or mailing, or they are sorted into totes assigned for delivery to a final destination such as a clinic or nursing home.

Figure 10:
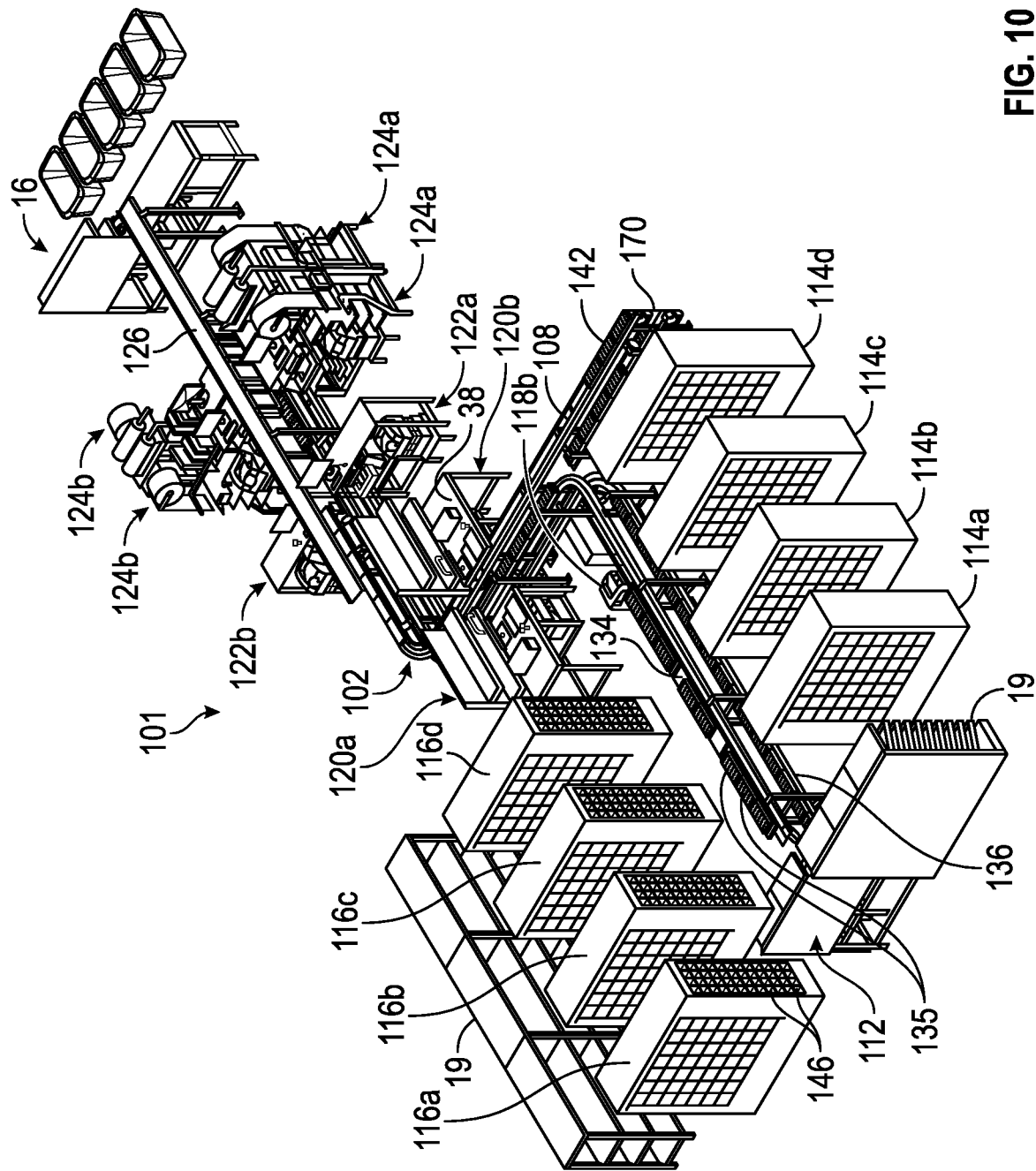
FIG. 10 is a perspective view of the countable product module of the embodiment shown in FIG. 8 with a shared manifest and shipping station.
Figure 11:
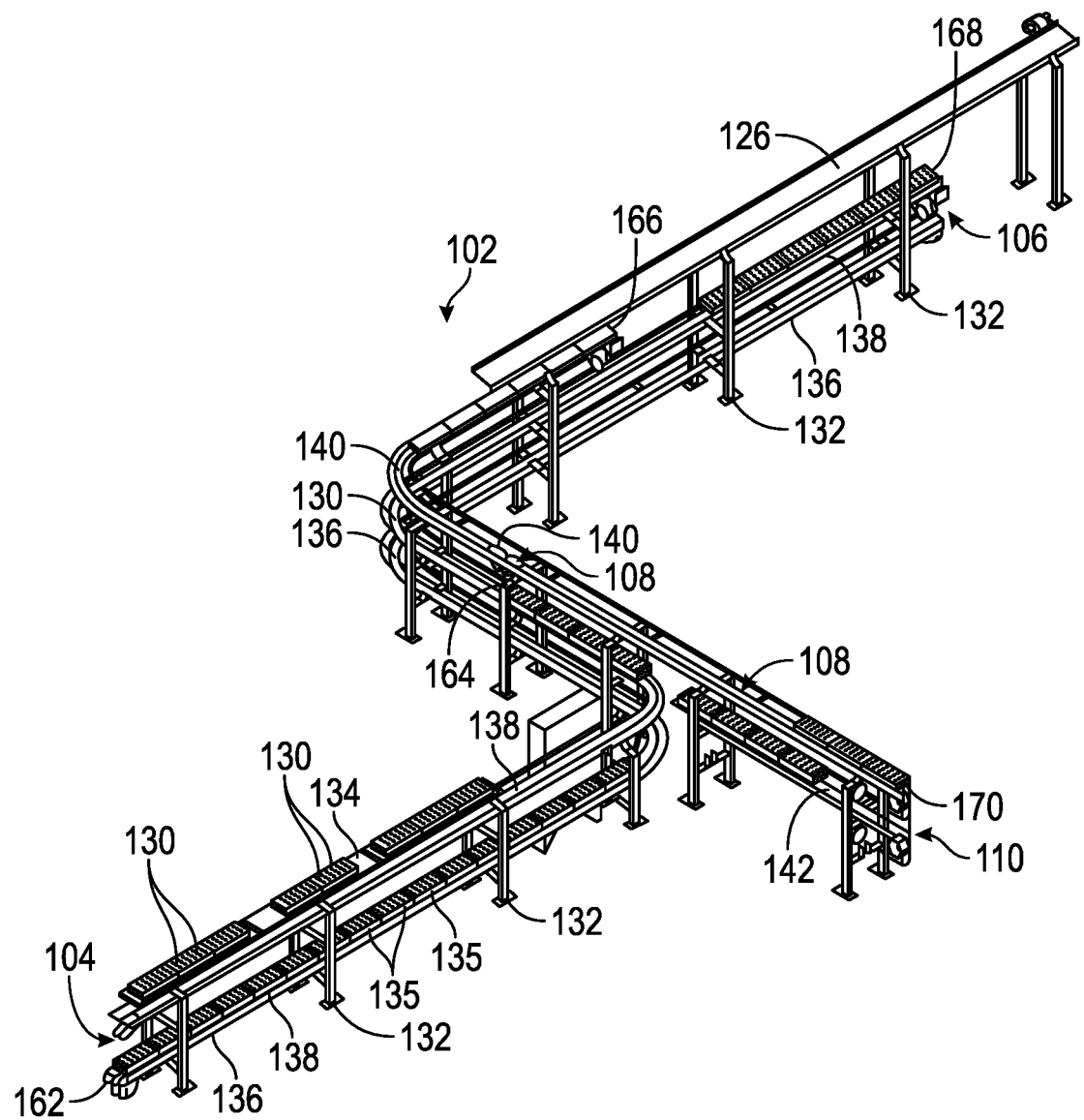
FIG. 11 is an enlarged perspective view of the central and package takeaway assemblies of the system module shown in FIG. 10.
Figure 12:
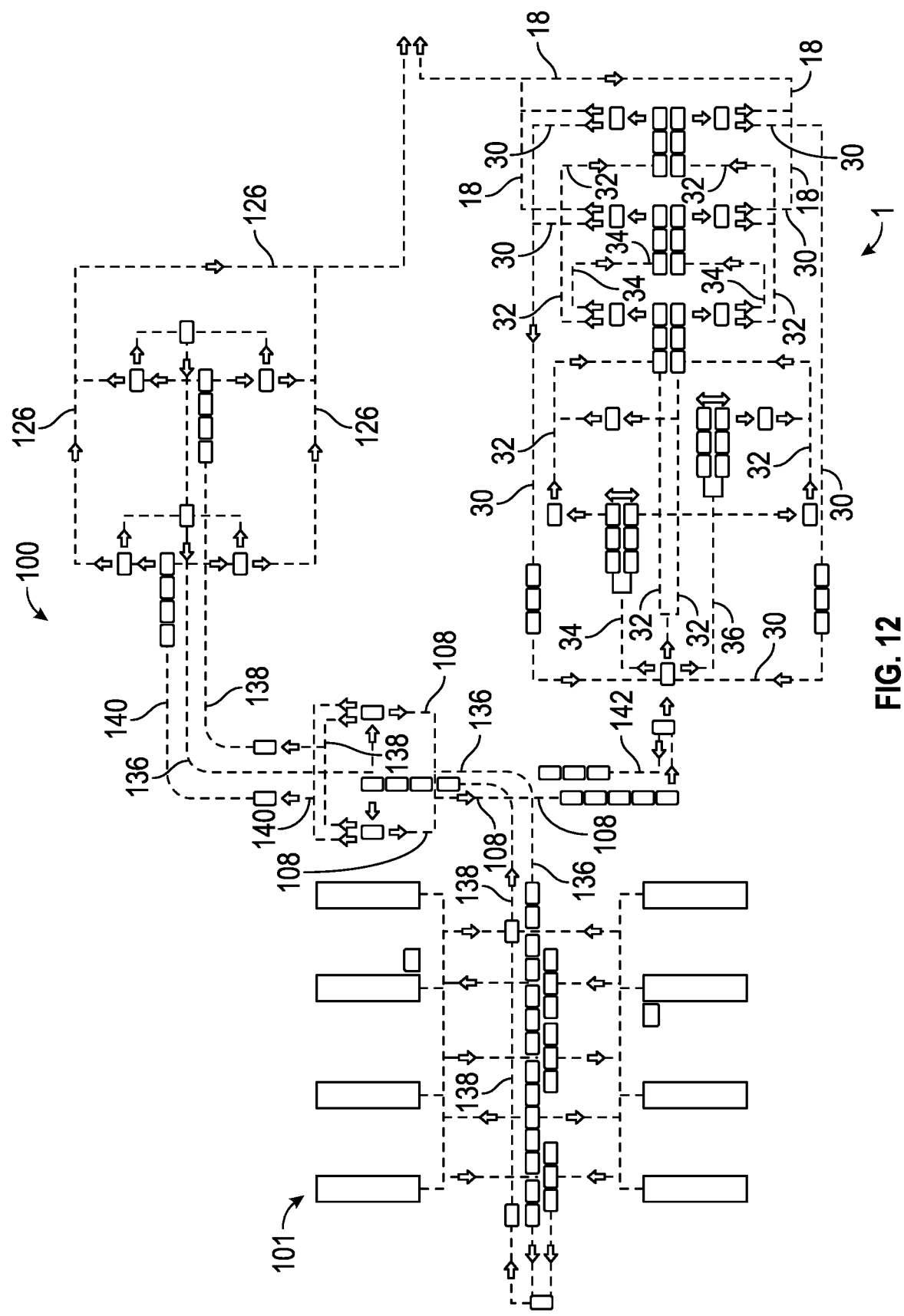
FIG. 12 is a flow diagram showing the sequence of movements and actions in accordance with the embodiment shown in FIG. 8.
Figure 13:
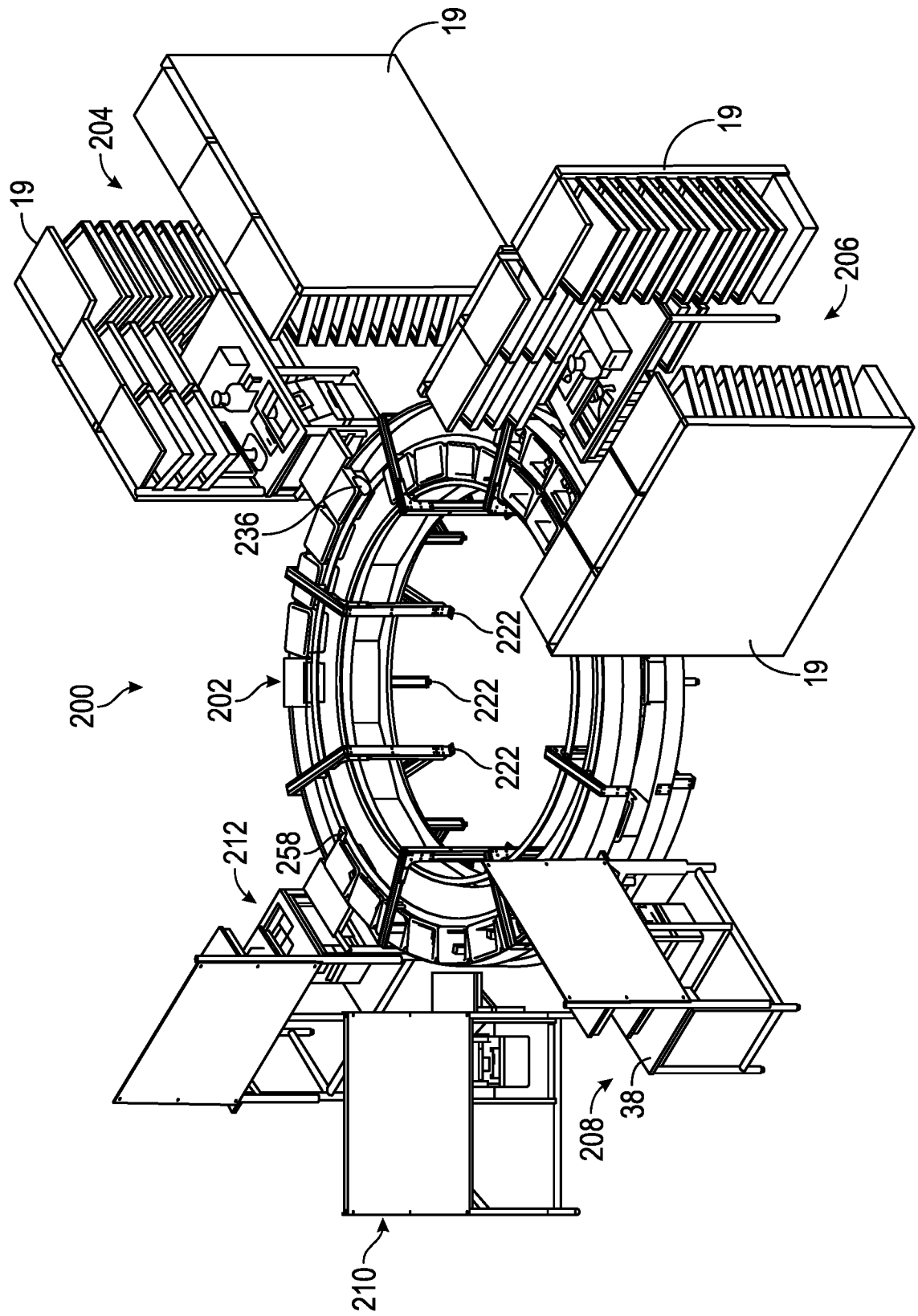
FIG. 13 is a perspective view of an embodiment of a modular product dispensing and verification system adapted for lower product throughput.

An alternate embodiment of a modular product dispensing and verification system 100 designed for greatly increased throughput is shown in FIGS. 8-12. The system 100 incorporates the system 1 and structures previously described as a module dedicated to dispensing, verifying and packaging unit-of-use items that may be refrigerated or kept at ambient temperature. The system 100 also includes a countables module 101 dedicated to dispensing, verifying and packaging countable items kept at ambient temperature. The countables module 101 includes a multilevel primary or central transporting conveyor assembly 102 for countable products that includes a first or dispensing end 104 and a second or packaging end 106. The central conveyor 102 has a generally serpentine overall configuration, with the upper level divided to form a rearward circulating transfer branch or spur 108 that extends generally transversely from the central conveyor. The transfer spur 108 is used for transporting orders from the countables module 101 to the unit-of-use/refrigerated module 1, and terminates in a conveyor third end 110 (FIG. 11).

A manual countable workstation 112 is positioned in spaced relation to the first end 104 of the central conveyor assembly 102, and the central conveyor 102 forms a spine bisecting two banks of robotic dispensing units 114a, 114b, 114c, 114d, and 116a, 116b, 116c, 116d, a pair of induction printers 118a, 118b, a pair of pharmacist verification stations 120a, 120b, a pair of single container packaging stations 122a, 122b, and a pair of multiple container packaging stations 124a, 124b, each station bank or pair disposed in spaced relation on opposite sides of the central conveyor 102 (FIG. 10). A package takeaway conveyor 126 connects the central conveyor 102 to the sortation and manifest station 16 of the dispensing system 1. High density storage units 19 as previously described in system 1 for storing countable products 130 and packaging are positioned in adjacent spaced relation to the robot dispensing stations 114a-d and 116a-d and the other stations as needed. Smaller storage units are positioned adjacent the manual countable dispensing station 112 and packaging station pairs 122a, 122b and 124a, 124b. The control system 1000 coordinates and controls operation of the system 100 including the countables module 101 and the system 1 module dedicated to unit-of-use and refrigerated products.

As best shown in FIG. 11, the central conveyor assembly 102 of the countables module 101 is a multi-tiered stack, including vertically spaced apart conveyors supported by a framework of single-support type conveyor frames 132. While the illustrated framework is constructed of multitier single-support type floor-mounted frames or stands, the conveyor assembly 102 may be supported in any suitable manner, including by overhead framework. The conveyor stack includes two tiers that extend between the first or dispensing end 104 and the area where the transfer spur 108 overlies a portion of the central conveyor. The two tiers also extend between the single container packaging station and the conveyor second end 102. Three tiers extend between the proximal end of the transfer spur 108 and the single container packaging station pair 122a, 122b. The transfer spur 108 of the conveyor assembly 108 is not continuous with the tier 3 central conveyor assembly 102, and operates independently in a reverse direction from the pharmacist verification stations 120a, 120b. A static platform or shelf 134 is mounted atop the conveyor frame supports 132 in the dispensing area between the first end of the conveyor 104 and the induction printers 118. The platform 134 provides a staging area for totes 135 to be delivered to the manual countable workstation 112, to one or more robots in the bank of robots 114a, 114b, 114c, 114d, or to one or more robots in the bank of robots 116a, 116b, 116c, 116d.

The first conveyor tier 136 is positioned at the lowermost or bottom level of the conveyor assembly 102. This tier 1 or tote return conveyor 136 transports returning empty totes 135 after the contents have been transferred to the package takeaway conveyor 126 at either the single container packaging stations 122a, 122b or the multiple container packaging stations 124a, 124b to the first or dispensing end of the conveyor assembly 104.

The second conveyor tier 138 is positioned in vertical spaced relation above the tier 1 conveyor 136. This tier 2 conveyor 138 transports orders having single containers of countable items as well as orders having multiple containers of countable items dispensed from the manual countable workstation 112 and/or the robot dispensing stations 114a, 114b, 1414c, 114d and 116a, 116b, 116c, 116d to the pharmacist verification stations 120a, 120b. The tier 2 conveyor 138 also transports orders having only multiple containers of countables from the verification stations 120a, 120b to the multiple container packaging stations 124a, 124b.

The third conveyor tier 140 is positioned in vertical spaced relation above the tier 2 conveyor 136. This conveyor tier is discontinuous at the verification stations 120a, 120b, with one section traveling forward in the direction of the second or packaging end 106 of the conveyor and the other traveling rearwardly in the direction of the third or transfer end 110 of the conveyor. The tier 3 conveyor 140 transports orders having only single containers of countables from the verification station pair 120a. 120b to the single container packaging stations 122a, 122b.

The rearward-traveling transfer spur 108 extends generally transversely from the central conveyor 102. This conveyor transports single or multiple countable orders that also specify unit-of-use items or that require refrigeration. These orders are transported to the transfer end 110 which is positioned adjacent the induction station 4 of the system 1 module. A forward circulating lower transfer tier 142 is positioned in vertical spaced relation below the transfer spur 108. This tier 142 is used as a transfer tote return for receiving empty totes from the operator of the induction station 4 after the transferred items have been placed in new totes for use in the system 1 module. The transfer tote return tier 142 transports the empty totes a short distance to a position adjacent the central conveyor assembly 102, where they are manually removed and deposited on the tier 1 tote return 136.

The package takeaway conveyor 126 extends upwardly at an angle from above the central conveyor 102 from the area of the single container packaging stations 122a, 122b and over the multiple container packaging stations 124a, 124b to the manifest and shipping station 16 which serves both the countables module 101 and the system 1 module.

At the dispensing end 104 of the countables module 101, the manual countables dispensing station 112 is positioned adjacent the first end 104 of the central conveyor 102. The dispensing station 112 is configured as previously described in system 1 to include a worktable 38 with document staging structure 44, keyboard 1016, monitor 1018, printer 39, counter 64, scanner 48, labeler 66 and product storage shelves 19. The control system 1000 transmits orders to the induction printer 39, which prints a dispensing itinerary 19 as previously described.

Depending on the order instructions, a dispensing workstation operator may remove an empty tote from the dispensing stop 162 of the conveyor tier 1 tote return 136 (FIG. 11), dispense the countable product into a container in accordance with the order and place the container in the tote, and deposit the tote onto conveyor tier 2 for transport directly to the verification stations 120a, 120b. Alternatively, the order instructions may require the operator to obtain a tote from a designated area on the platform staging area 134 to complete an order partially filled by one or more of the robot dispensing units 114a, 114b, 114c, 114d and/or 116a, 116b, 116c, 116d. The operator then dispenses the countable product into a container in accordance with the order and deposits the tote onto the tier 2 conveyor 138 for transport to verification stations 120a, 120b.

The robot induction printers 118a, 118b are positioned on either side of the central conveyor assembly 102 and receive patient orders transmitted by the control system 1000. Robot bank 114a, 114b, 114c, 114d includes corresponding adjacent dispensed medication accumulation areas 144a, 144b, 144c, 144d. Robot bank 116a, 116b, 116c, 116d includes corresponding adjacent dispensed medication accumulation areas 146a, 146b, 146c, 146d. The platform staging area 134 is adjacent the induction printers 118a, 118b and includes discrete areas for totes designated for completion by manual dispensing, delivery to one or more robots or for manual transfer between specific robots.

A dispensing workstation operator obtains the printed order and obtains an empty tote from the tote queue at dispensing stop 164 or obtains from the staging area 134 a tote that has been partially filled by one or more robots from the opposite robot bank 114a, 114b, 114c, 114d or 116a, 116b, 116c, 116d and transfers the tote to the next robot designated on the order. Once robot dispensing has been completed, the operator reviews the printed itinerary and, if the order has been completed, deposits the tote on the tier 2 conveyor 138 for delivery to the verification stations 120a, 120b. If robot dispensing has not completed the order and additional manual dispensing is required, the operator transfers the tote to the manual countable workstation 112 for completion.

The tier 2 conveyor 138 transports all completed dispensed orders and document sets 19 to the verification stop 164 at the pharmacist verification station pair 120a, 120b. The verification workstation station pair is configured as previously described to include a work table 38, staging structure 44, keyboard 1016, monitor 1018, printer 39, counter 64, scanner 48, labeler 66, and storage shelves 19.

A pharmacist at the pharmacist verification workstation removes a tote 135 from the queue at the verification stop 164, transfers it to the work table 38, and scans the document itinerary barcode. This causes the computer display unit 1018 to display the order information. The pharmacist verifies each container in the tote carrier, one by one. As the label on each item is scanned, the display unit 1018 provides details of the prescription and product images (if available). Once a container has been verified, the pharmacist actuates a function key on the keyboard 1016. After all items have been verified, the display unit 1018 prompts the pharmacist to deposit the tote onto either the tier 2 conveyor 138 for transport to the multiple container packaging stations 124a, 124b, onto the tier 3 conveyor 140 for transport forward to the single container packaging stations 122a, 122b, or onto the rearward circulating tier 3 transfer spur 108 for transfer to the system 1 module for additional dispensing of unit-of-use products and/or for cold chain packaging.

The tier 3 conveyor 140 transports all verified, completed single container orders, that is, single container orders having document sets 19 that do not require further processing by the system 1 module, to the single container packaging stop 166. The single container packaging station pair 122a, 122b includes a worktable 38 including staging structure 44, keyboard 1016, monitor 1018, printer 39, scanner 48, labeler 66, and storage shelves 19.

A packaging workstation operator removes a tote from the queue at the single container packaging stop 166, transfers it to the worktable 38, and scans the document itinerary barcode. This actuates the display unit 1018 to display the order information. The operator then scans the prescription label on the container. Once the control system 1000 has verified the order status as ready for packaging, it actuates the document printer 39 to print a patient-specific literature pack, checks that the scanned item matches the order item(s), actuates the label printer 66. The operator is prompted to apply the printed label to a new, empty package or bag and scan the barcode on the label. The control system 1000 verifies that the barcode on the label matches the order, and the display unit 1018 prompts the operator to seal the package and deposit it onto the package takeaway conveyor 126. The operator then deposits the empty tote onto the tier 1 return tote conveyor 136 for return to the dispensing stop 162.

If the control system 1000 determines a mismatch, that is, a scanned item that does not belong in the order, or if a prescription status is incorrect, the display unit 1018 displays an error message including instructions to the packer to discard any printed documents and requiring a supervisor to enter a password to clear the error. If the error is attributable to incorrect scanning, the packer re-processes the items from the tote. If the error is attributable to missing/additional/incorrect items or incorrect prescription status, the packer hands off the tote to an exceptions worker and proceeds with the next tote.

The tier 3 transfer branch 108 conveyor transports to the transfer stop 170 all countable dispensed orders and document sets 19 requiring further processing by the system 1 module, that is, orders requiring dispensing of unit-of-use products and/or cold chain packaging. The transfer stop 170 is located adjacent the system 1 document induction workstation 4. A document induction operator removes a tote 135 from the queue at the stop 170 and transfers it to the induction workstation 4 for induction into the system 1 module.

The Tier 2 conveyor 138 transports to the multiple container packaging stop 168 all verified, completed multiple container orders, that is, multiple container orders having document sets 19 that do not require further processing by the system 1 module. The multiple container packaging station pair 124a, 124b is configured as previously described to include a worktable 38, with staging structure 44, keyboard 1016, monitor 1018, printer 39, scanner 48, labeler 66, and storage shelves 19.

A packaging workstation operator removes a tote from the queue at the packaging stop 168, transfers it to the worktable 38, and scans the document itinerary barcode. This actuates the display unit 1018 to display the order information. The operator then collects the contents of the tote and scans each of the prescription labels. Once the control system 1000 has verified the order status as ready for packaging, it actuates the document printer 39 to print a patient-specific literature pack, checks that the scanned item matches the order item(s), actuates the label printer 66. The packer is prompted to apply the printed label to a new, empty package or bag and scan the barcode on the label. The control system 1000 verifies that the barcode on the label matches the order, and the display unit 1018 prompts the operator to seal the package and deposit it onto the package takeaway conveyor 126. The operator then deposits the empty tote onto the tier 1 conveyor 136 for return to the product dispensing stop 162. If the control system 1000 determines a mismatch, it is processed as previously described.

The package takeaway conveyor 126 transports the packages to the shared system 1 module manifest and shipping station 16, where operators remove the packages from the conveyor and process them as previously described.

Figure 14:
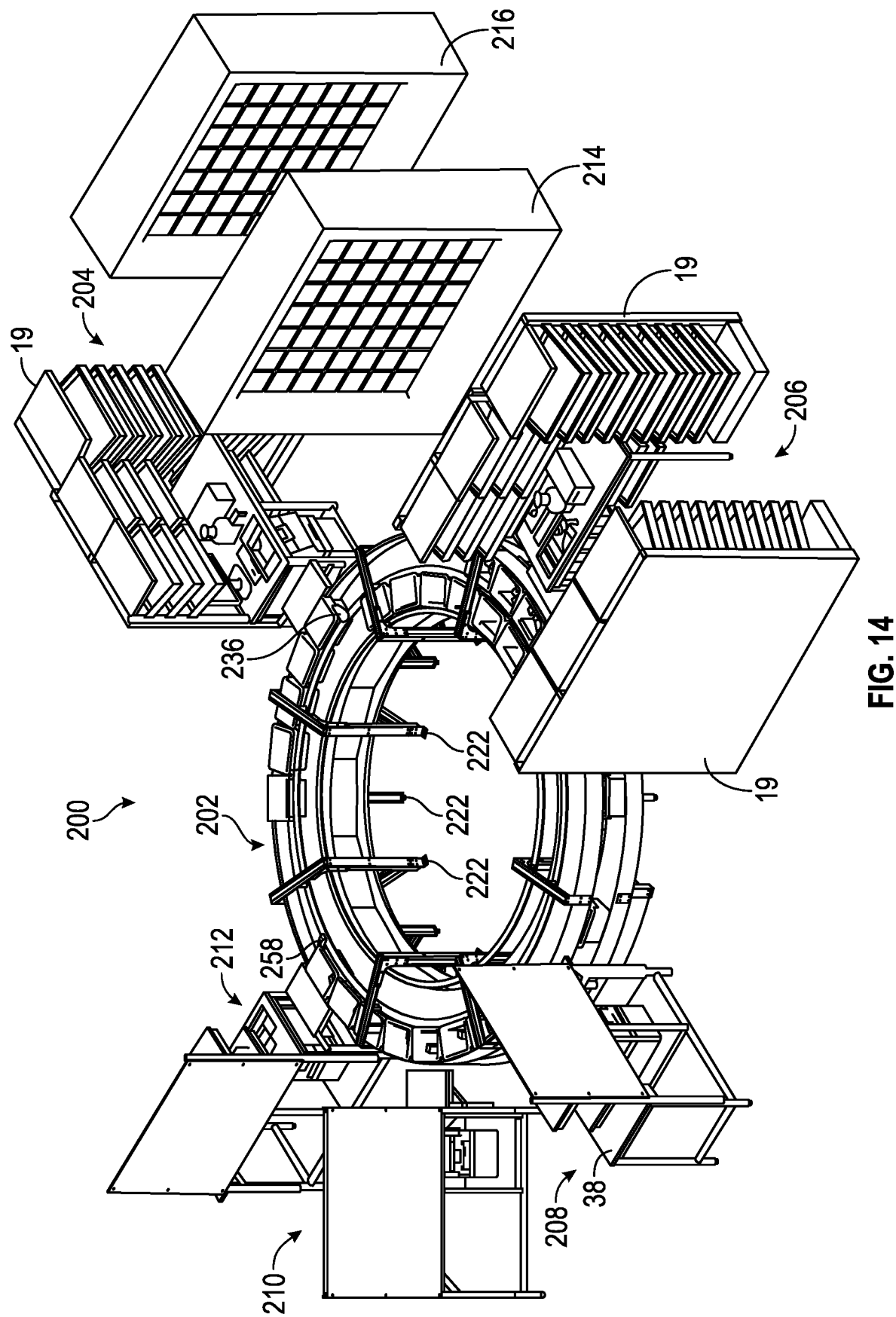
FIG. 14 is a perspective view of the system shown in FIG. 13 configured to include robot dispensing units.
Figure 15:
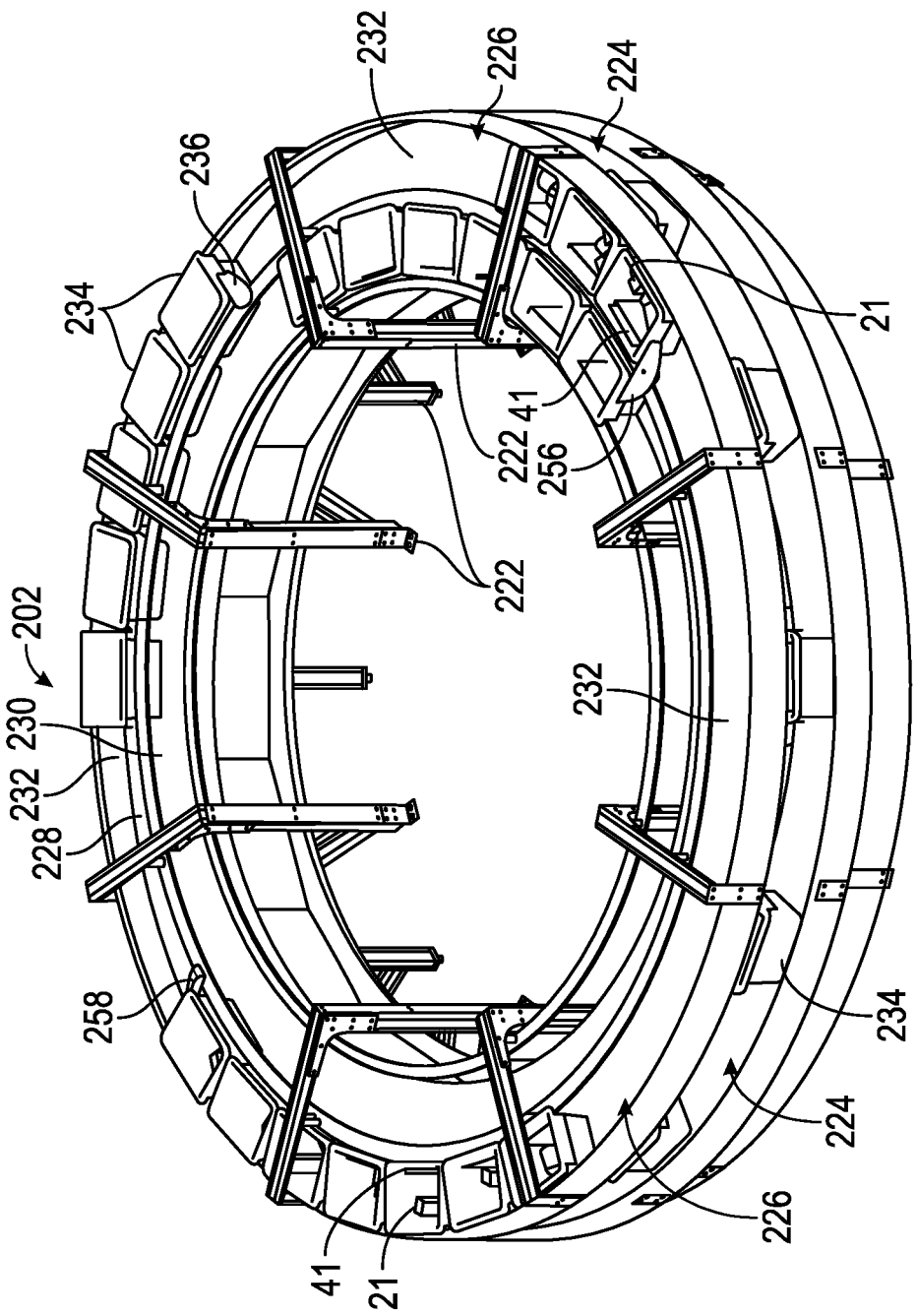
FIG. 15 is an enlarged perspective view of the conveyor assembly shown in FIG. 13.
Figure 16:
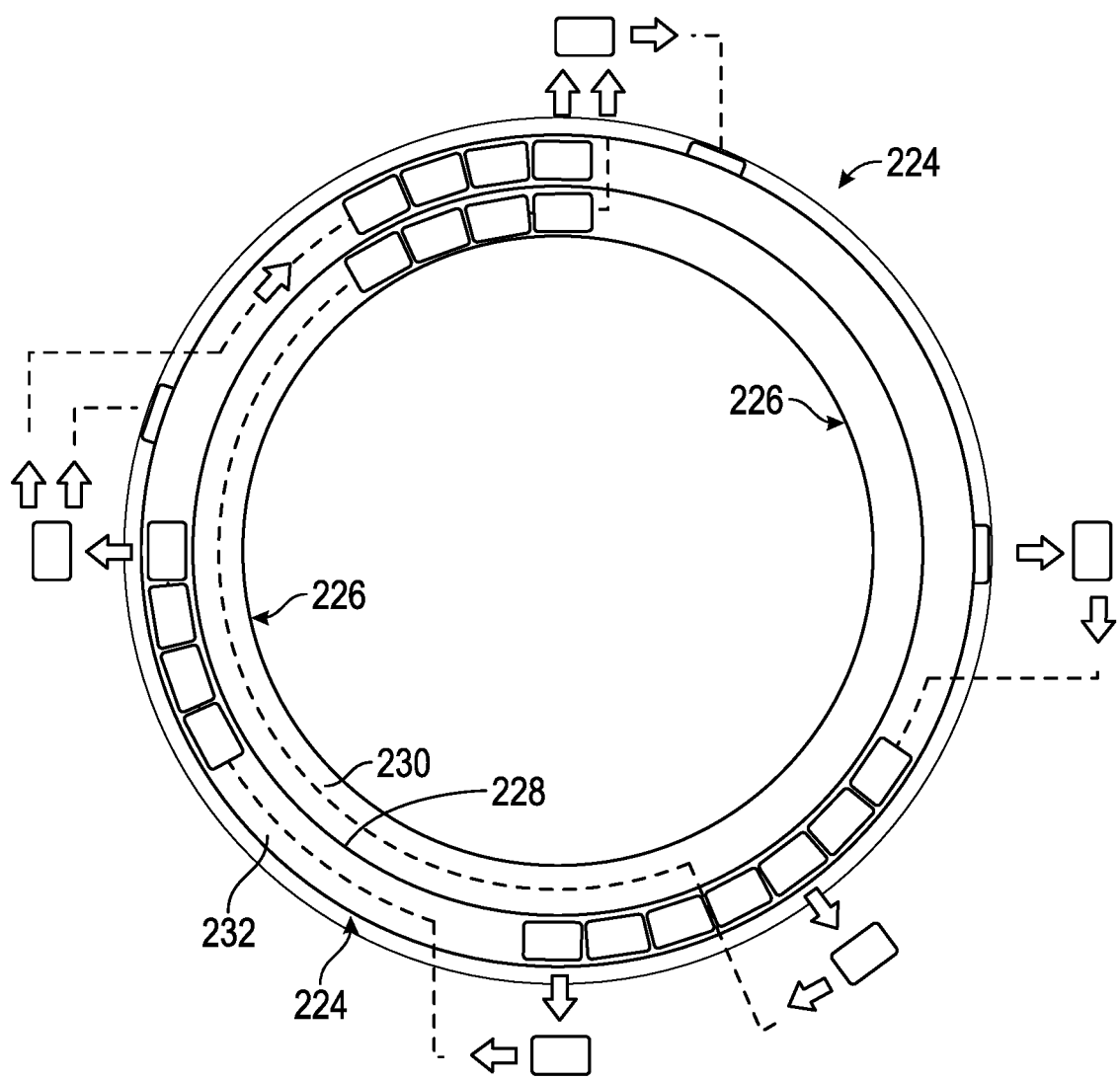
FIG. 16 is a flow diagram showing the sequence of movements and actions in accordance with the embodiment shown in FIG. 13.

Another embodiment of a modular product dispensing and verification system 200 designed for lower product throughput is illustrated in FIGS. 13-16. The system 200 includes a multilevel, transport conveyor assembly 202 having a generally circular overall configuration. The conveyor assembly 202 is configured in the form of a ring, with first and second manual dispensing workstations 204 and 206, a pharmacist verification workstation 208, and first and second packaging workstations 210 and 212 positioned in spaced relation around the outer perimeter of the ring. The dispensing stations 204 and 206 may also be configured to include one or more optional robotic dispensing units 214 and 216 (FIG. 14). The workstations are configured as previously described to include a worktable 38 with document staging structure 44, keyboard 1016, monitor 1018, printer 39, counter 64, a scanner 48, labeler 66 as needed (FIG. 3). High density storage shelves 19 for storing products 21 and packaging materials are positioned in adjacent spaced relation to the stations as needed. It is foreseen that the system 200 may be sized and configured to include one or a plurality of each type of workstation as needed.

The conveyor assembly ring 202 includes a two tiered stack including vertically spaced apart conveyors supported in a single-support type conveyor frame 222. The first conveyor tier 224 is positioned at the lowermost or bottom level of the conveyor assembly 202. The tier 1 conveyor 224 transports totes 234 containing dispensed products 21 in a continuous loop until removed at the verification station 208 for verification. The second conveyor tier 226 is positioned in vertical spaced relation above the tier 1 conveyor 224. The tier 2 conveyor 226 is used to transfer empty totes from the packaging stations to the dispensing stations 204 and 206, and from the first dispensing station 204 to the second dispensing station 206. The tier 2 conveyor also transports totes containing verified products from the verification station 208 to the packaging stations 210 and 212.

The first dispensing station 204 is positioned adjacent a first dispensing stop 236 located in the adjacent outer lane 232 of the upper conveyor 226. Empty totes from the packaging station 212 queue up at this stop in the outer lane for use by the dispensing station 204.

The control system 1000 transmits orders to the induction printer 242, which prints a routing and dispensing itinerary 41 as previously described. The operator removes an empty tote from the queue at the stop 236, dispenses the product in accordance with the order, labels it and places the product(s) into the tote. Where the first dispensing station 204 includes one or more robot dispensing units, in addition to the orders transmitted to the induction printer 242, the control system 1000 transmits instructions to one or both robot units 214 and 216 to dispense products in accordance with the order. These products are deposited by the robot units into a respective robot staging area 254 that is connected to each dispensing units 214 and 216. When the induction printer prints an order that specifies products from one or both of the robot dispensing units, the order indicates the location of the product in the respective robot staging area. The operator dispenses any manual dispensable products specified by the order, collects any robot-dispensable products specified, and deposits all of the products in an empty tote.

If the order is complete, the operator places the tote with the document set on the lower conveyor 224 for transport directly to the pharmacist verification station 208. If additional products are required from the second dispensing station 206, the operator deposits the tote and document set beyond the stop 236 in the outer lane 232 of the upper conveyor 226 for transport to the second dispensing station 206.

The second dispensing station 206 is positioned adjacent a second dispensing stop 256 located in both the adjacent inner and outer lanes 230 and 232 of the upper conveyor 226. Empty totes from the packaging station 212 queue up in the inner lane 230 and totes containing orders partially filled at the first dispensing station 204 queue up in the outer lane 232 at the stop 256.

The second dispensing station operator removes a tote containing a partially filled order from the outer lane 232 queue at the stop 256, dispenses and labels one or more additional products in accordance with the order, deposits the one or more labeled products into the tote and deposits the tote onto the tier 1 conveyor 224 for transport to the pharmacist verification station 208. Where orders are to be filled entirely at the second dispensing station 206, the control system 1000 transmits the order to the station induction printer, which prints a routing and dispensing itinerary 41 as previously described. The operator removes an empty tote from the inner lane 230 queue at the stop 256, dispenses one or more products in accordance with the order, labels and places the product(s) into the tote. The operator then deposits the tote with the document set on the tier 1 conveyor 224 for transport to the pharmacist verification station 208.

The tier 1 conveyor 224 transports all completed, dispensed orders and their dispensing itineraries 41 to the pharmacist verification station 208. The lower conveyor tier 224 includes no stops, so the totes 234 circulate clockwise on this tier. The pharmacist removes a tote from the tier 224, transfers it to the work table 238, and scans the document itinerary barcode. This causes the computer display unit 1018 to display the order information. The pharmacist verifies each product in the tote. As the label on each item is scanned, the display unit 1018 provides details of the prescription. The pharmacist actuates a function key on the keyboard 1016 after each product has been verified. After all products in the tote have been verified, the pharmacist deposits the tote and its document itinerary in the outer lane 232 of the upper conveyor 226 for transport to the packaging stations 210 and 212.

Both packaging stations are served by a single stop 258, which is positioned adjacent the second packaging station 212. Totes travel in the outer lane 232 and form a queue behind the stop 258.

The operator at the second packaging station 212 removes the first tote in the queue. The operator at the first packaging station 210 removes a tote from the queue adjacent the station 210. Each station operator transfers a tote to the respective station worktable 38 and scans the document itinerary barcode. This actuates the display unit 1018 to display the order information. The operator then scans the label of each product in the tote. Once the control system has verified the order status as ready for packaging, it actuates the printer 242 to print a patient-specific literature pack, verifies that the scanned products match the order item(s) listed on the itinerary, and actuates the label printer 66. The operator is prompted to apply the printed label to a new, empty package or bag and to scan the barcode on the label. The control system 1000 verifies that the barcode on the label matches the order, and the display unit 1018 prompts the operator to seal the package and deposit it into an adjacent bin (not shown) for later delivery. The operator then deposits the empty tote onto the conveyor upper tier 226, for return to a dispensing station 204 or 206. The operator of the first packaging station 210 deposits empty totes on the inner lane 230 for travel to the empty tote queue at the second dispensing station stop 256. The operator of the second packaging station 212 deposits empty totes on the outer lane 232 for travel to the empty tote queue at the first dispensing station stop 236.

Operation of the various components of the modular product dispensing and verification system embodiments 1, 10, 0 and 200 is coordinated by an exemplary control system illustrated in FIG. 7. The control system is shown in the form of a computing system 1000 that may implement various systems such as the product dispensing system and the method discussed herein. A general purpose computer system 1000 is capable of executing a computer program product to execute a computer process. Data and program files may be input to the computer system 1000, which reads the files and executes the programs therein. Some of the elements of a general purpose computer control system 1000 are shown in FIG. 7 wherein a computer or processor 1002 is shown having an input/output (I/O) section 1004, a central processing unit (CPU) 1006, and a memory section 1008. There may be one or more processors 1002, such that the processor 1002 of the computer system 1000 comprises a single central-processing unit 1006, or a plurality of processing units, commonly referred to as a parallel processing environment. The computer system 1000 may be a conventional computer, a server, a distributed computer, or any other type of computer, such as one or more external computers made available via a cloud computing architecture. The presently described technology is optionally implemented in software devices loaded in memory 1008, stored on a configured DVD/CD-ROM 1010 or storage unit 1012, and/or communicated via a wired or wireless network link 1014, thereby transforming the computer system 1000 in FIG. 3 to a special purpose machine for implementing the described operations.

The memory section 1008 may be volatile media, non-volatile media, removable media, non-removable media, and/or other media or mediums that can be accessed by a general purpose or special purpose computing device. For example, the memory section 1008 may include non-transitory computer storage media and communication media. Non-transitory computer storage media further may include volatile, nonvolatile, removable, and/or non-removable media implemented in a method or technology for the storage (and retrieval) of information, such as computer/machine-readable/executable instructions, data and data structures, engines, program modules, and/or other data. Communication media may, for example, embody computer/machine-readable/executable, data structures, program modules, algorithms, and/or other data. The communication media may also include an information delivery technology. The communication media may include wired and/or wireless connections and technologies and be used to transmit and/or receive wired and/or wireless communications.

The I/O section 1004 is connected to one or more user-interface devices (e.g., a keyboard 1016 and a display unit 1018), a disc storage unit 1012, and a disc drive unit 1020. Generally, the disc drive unit 1020 is a DVD/CD-ROM drive unit capable of reading the DVD/CD-ROM medium 1010, which typically contains programs and data 1022. Computer program products containing mechanisms to effectuate the systems and methods in accordance with the presently described technology may reside in the memory section 1004, on a disc storage unit 1012, on the DVD/CD-ROM medium 1010 of the computer system 1000, or on external storage devices made available via a cloud computing architecture with such computer program products, including one or more database management products, web server products, application server products, and/or other additional software components. Alternatively, a disc drive unit 1020 may be replaced or supplemented by a tape drive unit, or other storage medium drive unit. The network adapter 1024 is capable of connecting the computer system 1000 to a network via the network link 1014, through which the computer system can receive instructions and data. Examples of such systems include personal computers, Intel or PowerPC-based computing systems, AMD-based computing systems, ARM-based computing systems, and other systems running a Windows-based, a UNIX-based, or other operating system. It should be understood that computing systems may also embody devices such as Personal Digital Assistants (PDAs), mobile phones, tablets or slates, multimedia consoles, gaming consoles, set top boxes, etc.

When used in a LAN-networking environment, the computer system 1000 is connected (by wired connection and/or wirelessly) to a local network through the network interface or adapter 1024, which is one type of communications device. When used in a WAN-networking environment, the computer system 1000 typically includes a modem, a network adapter, or any other type of communications device for establishing communications over the wide area network. In a networked environment, program modules depicted relative to the computer system 1000 or portions thereof, may be stored in a remote memory storage device. It is appreciated that the network connections shown are examples of communications devices for and other means of establishing a communications link between the computers may be used.

In an exemplary implementation, stored source code may be embodied by instructions stored on such storage systems such as the disc storage unit 1012 or the DVD/CD-ROM medium 1010, and/or other external storage devices made available and accessible via a network architecture, and executed by the processor 1002.

Some or all of the operations described herein may be performed by the processor 1002, which is hardware. Further, local computing systems, remote data sources and/or services, and other associated logic represent firmware, hardware, and/or software configured to control operations of the robotic dispensing units and/or other components. Such services may be implemented using a general purpose computer and specialized software (such as a server executing service software), a special purpose computing system and specialized software (such as a mobile device or network appliance executing service software), or other computing configurations. In addition, one or more functionalities disclosed herein may be generated by the processor 1002 and a user may interact with a Graphical User Interface (GUI) using one or more user-interface devices (e.g., the keyboard 1016, the display unit 1018, and the user devices 1004) with some of the data in use directly coming from online sources and data stores. The system set forth in FIG. 3 is but one possible example of a computer system that may employ or be configured in accordance with aspects of the present disclosure.

In the present disclosure, certain of the automated methods disclosed may be implements as sets of instructions or software readable by a device. Further, it is understood that the specific order or hierarchy of steps in the automated and manual methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described control system may be provided as a computer program product, or software, that may include a non-transitory machine-readable medium having stored thereon executable instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may include, but is not limited to, optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic executable instructions.

Advantageously, the modular product dispensing and verification system provides a dispensing and verification system in kit form, that allows for addition or deletion of pairs of document induction, dispensing, verification and packaging workstations to accommodate workflow needs. A dispensary may at first employ the system 200 and may add robotic dispensing unit, additional manual dispensing stations, verification, and packaging stations until throughput needs exceed the system capacity. The dispensary may then remove the transport conveyor ring 202 and replace it with a primary conveyor assembly 2, to obtain the system 1 embodiment, adding additional robots, manual dispensing, verification, and packaging stations as needed. When throughput needs exceed the capacity of the system 1, the conveyor assembly 102 may be acquired, and the system 1 embodiment dedicated to dispensing unit-of-use and pre-packaged items and items requiring refrigeration, and used in conjunction with the conveyor assembly 102 and additional operating stations as a module dedicated to dispensing countable items at ambient temperature to achieve high throughput. Additional workstations may be added to each module as needed to further increase throughput.

All modules of the system also allow for transfer of a completed dispensed order directly from a manual dispensing station or a robot dispensing unit directly to a verification station, without diverting the completed order into one or more additional and unnecessary dispensing station queues. It is foreseen that the central conveyors and pairs of adjacent workstations may be arranged in a ring, a straight line, or in any other geometric configuration suitable for the available workspace. Such configurations need not involve straight runs of the conveyor tiers, but may instead involve curvate configurations, and/or configurations in which one or more workstations and the associated conveyor tiers are in an orthogonal or angular relation to the spine of the central conveyor.

The description above includes exemplary systems, methods, techniques, instruction sequences, and/or computer program products that embody techniques of the present disclosure. However, it is understood that the described disclosure may be practiced without these specific details.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. A system comprising:
    at least one processor;
    an ambient countable module comprising:
        a central conveyor comprising a first transport conveyor, a second transport conveyor vertically spaced above the first transport conveyor, and a third transport conveyor vertically spaced above the second transport conveyor;
        a rearward traveling transfer branch extending generally transversely from the central conveyor;
        a product dispensing station comprising a single container packaging station and a multiple container packaging station; and
    a computer-readable storage device storing instructions which, when executed by the at least one processor, cause the at least one processor to:
        receive a patient order for a medication;
        activate the second transport conveyor to transport the patient order from the product dispensing station to a verification station;
        if the patient order does not require further processing by a special module of the system,
        activate the second transport conveyor to transport the patient order having two or more containers from the verification station to the multiple container packaging station or
        activate the third transport conveyor to transport the patient order having a single container from the verification station to the single container packaging station; and
        if the patient order requires further processing by the special module,
        activate the rearward traveling transfer branch to transport the patient order to a transfer stop where the special module is located nearby.

2. The system of claim 1, wherein each of the first transport conveyor, second transport conveyor, and third transport conveyor extends between a proximal end of the rearward traveling transfer branch and the single container packaging station.

3. The system of claim 1, wherein each of the first transport conveyor and second transport conveyor extends between a dispensing end near the product dispensing station and an area where the rearward traveling transfer branch overlies a portion of the central conveyor.

4. The system of claim 3, wherein the first transport conveyor, after contents in totes are transferred to a package takeaway conveyor at the single container packaging station or the multiple container packaging station, transports empty totes to the dispensing end.

5. The system of claim 4, wherein the package takeaway conveyor connects between the central conveyor and a shipping station positioned near a packaging end.

6. The system of claim 1, wherein the rearward traveling transfer branch is discontinuous from the third transport conveyor of the central conveyor and is configured to operate independently from the central conveyor in a reverse direction from the verification station.

7. The system of claim 1, wherein the rearward traveling transfer branch terminates at a conveyor end and transfers the patient order from the ambient countable module to the special module for refrigerated products.

8. A method for increasing throughput in dispensing, verifying, and packaging, the method comprising:
receiving a patient order for a medication in a system comprising:
at least one processor;
an ambient countable module comprising:
a central conveyor comprising a first transport conveyor, a second transport conveyor vertically spaced above the first transport conveyor, and a third transport conveyor vertically spaced above the second transport conveyor;
a rearward traveling transfer branch extending generally transversely from the central conveyor;
a product dispensing station comprising a single container packaging station and a multiple container packaging station;
activating the second transport conveyor to transport the patient order from the product dispensing station to a verification station;
if the patient order does not require further processing by a special module of the system,
activating the second transport conveyor to transport the patient order having two or more containers from the verification station to the multiple container packaging station or
activating the third transport conveyor to transport the patient order having a single container from the verification station to the single container packaging station; and
if the patient order requires further processing by the special module,
activating the rearward traveling transfer branch to transport the patient order to a transfer stop where the special module is located nearby.

9. The method of claim 8, wherein each of the first transport conveyor, second transport conveyor, and third transport conveyor extends between a proximal end of the rearward traveling transfer branch and the single container packaging station.

10. The method of claim 8, wherein each of the first transport conveyor and second transport conveyor extends between a dispensing end near the product dispensing station and an area where the rearward traveling transfer branch overlies a portion of the central conveyor.

11. The method of claim 10, further comprising:
transferring contents in totes to a package takeaway conveyor at the single container packaging station or the multiple container packaging station; and
transporting empty totes, by the first transport conveyor, to the dispensing end.

12. The method of claim 11, wherein the package takeaway conveyor connects between the central conveyor and a shipping station positioned near a packaging end.

13. The method of claim 8, wherein the rearward traveling transfer branch is discontinuous from the third transport conveyor of the central conveyor and is configured to operate independently from the central conveyor in a reverse direction from the verification station.

14. The method of claim 8, wherein the rearward traveling transfer branch terminates at a conveyor end and transfers the patient order from the ambient countable module to the special module for refrigerated products.

15. A non-transitory computer-readable storage medium having instructions stored thereon that, when executed by at least one processor, cause the at least one processor to perform operations, comprising:
receiving a patient order for a medication in a system comprising:
at least one processor;
an ambient countable module comprising:
a central conveyor comprising a first transport conveyor, a second transport conveyor vertically spaced above the first transport conveyor, and a third transport conveyor vertically spaced above the second transport conveyor;
a rearward traveling transfer branch extending generally transversely from the central conveyor;
a product dispensing station comprising a single container packaging station and a multiple container packaging station;
activating the second transport conveyor to transport the patient order from the product dispensing station to a verification station;
if the patient order does not require further processing by a special module of the system,
activating the second transport conveyor to transport the patient order having two or more containers from the verification station to the multiple container packaging station or
activating the third transport conveyor to transport the patient order having a single container from the verification station to the single container packaging station; and
if the patient order requires further processing by the special module,
activating the rearward traveling transfer branch to transport the patient order to a transfer stop where the special module is located nearby.

16. The non-transitory computer-readable storage medium of claim 15, wherein each of the first transport conveyor, second transport conveyor, and third transport conveyor extends between a proximal end of the rearward traveling transfer branch and the single container packaging station.

17. The non-transitory computer-readable storage medium of claim 15, wherein each of the first transport conveyor and second transport conveyor extends between a dispensing end near the product dispensing station and an area where the rearward traveling transfer branch overlies a portion of the central conveyor.

18. The non-transitory computer-readable storage medium of claim 17, wherein the non-transitory computer-readable storage medium comprises instructions stored thereon that, when executed by at least one processor, cause the at least one processor to:

transfer contents in totes to a package takeaway conveyor at the single container packaging station or the multiple container packaging station; and transport empty totes, by the first transport conveyor, to the dispensing end.

19. The non-transitory computer-readable storage medium of claim 18, wherein the package takeaway conveyor connects between the central conveyor and a shipping station positioned near a packaging end.

20. The non-transitory computer-readable storage medium of claim 15, wherein the rearward traveling transfer branch is discontinuous from the third transport conveyor of the central conveyor and is configured to operate independently from the central conveyor in a reverse direction from the verification station, wherein the rearward traveling transfer branch terminates at a conveyor end and transfers the patient order from the ambient countable module to the special module for refrigerated products.

* * * * *